(12) United States Patent
Klymchenko et al.

(10) Patent No.: US 12,291,654 B2
(45) Date of Patent: May 6, 2025

(54) FLUORESCENT POLYMERIC COATING FILM FOR MEDICAL DEVICES

(71) Applicants: UNIVERSITE DE STRASBOURG, Strasbourg (FR); CENTRE NATIONAL DE LA RECHERCHE SCIENTIFIQUE, Paris (FR); INSTITUT HOSPITALO-UNIVERSITAIRE DE CHIRURGIE MINI-INVASIVE GUIDEE PAR L'IMAGE, Strasbourg (FR); INSTITUT DE RECHERCHE CONTRE LES CANCERS DE L'APPAREIL DIGESTIF (IRCAD), Strasbourg (FR)

(72) Inventors: Andrey Klymchenko, Illkirch (FR); Bohdan Andreiuk, Illkirch-Graffenstaden (FR); Seong-Ho Kong, Seoul (KR); Michele Diana, Lingolsheim (FR); Renato Soares, Parana (BR)

(73) Assignees: UNIVERSITE DE STRASBOURG, Strasbourg (FR); CENTRE NATIONAL DE LA RECHERCHE SCIENTIFIQUE, Paris (FR); INSTITUT HOSPITALO-UNIVERSITAIRE DE CHIRURGIE MINI-INVASIVE GUIDEE PAR L'IMAGE, Strasbourg (FR); INSTITUT DE RECHERCHE CONTRE LES CANCERS DE L'APPAREIL DIGESTIF (IRCAD), Strasbourg (FR)

( * ) Notice: Subject to any disclaimer, the term of this patent is extended or adjusted under 35 U.S.C. 154(b) by 1194 days.

(21) Appl. No.: 16/964,704

(22) PCT Filed: Jan. 28, 2019

(86) PCT No.: PCT/EP2019/051990
§ 371 (c)(1),
(2) Date: Jul. 24, 2020

(87) PCT Pub. No.: WO2019/145532
PCT Pub. Date: Aug. 1, 2019

(65) Prior Publication Data
US 2020/0347243 A1 Nov. 5, 2020

(30) Foreign Application Priority Data
Jan. 26, 2018 (EP) .................... 18305075

(51) Int. Cl.
C09D 5/22 (2006.01)
A61B 17/06 (2006.01)
A61M 25/00 (2006.01)
C09B 23/01 (2006.01)
C09B 23/08 (2006.01)
C09D 7/20 (2018.01)
C09D 133/12 (2006.01)
C09K 11/06 (2006.01)

(52) U.S. Cl.
CPC .......... *C09D 5/22* (2013.01); *A61B 17/06166* (2013.01); *A61M 25/0045* (2013.01); *C09B 23/0066* (2013.01); *C09B 23/083* (2013.01); *C09D 7/20* (2018.01); *C09D 133/12* (2013.01); *C09K 11/06* (2013.01); *C09K 2211/1007* (2013.01); *C09K 2211/1018* (2013.01)

(58) Field of Classification Search
CPC .... C09B 23/0066; C09B 23/08; C09B 23/083
See application file for complete search history.

(56) References Cited

U.S. PATENT DOCUMENTS

| | | | | |
|---|---|---|---|---|
| 2003/0113655 | A1* | 6/2003 | Hayakawa | ............ G03F 7/0382 430/944 |
| 2011/0067387 | A1 | 3/2011 | Jacques et al. | |

FOREIGN PATENT DOCUMENTS

| | | |
|---|---|---|
| JP | S5967092 A | 4/1984 |
| JP | S59201243 A | 11/1984 |
| WO | 2017/151634 A1 | 9/2017 |

OTHER PUBLICATIONS

Machine translation of JPS5967092 (Year: 1984).*
International Search Report and Written Opinion of the International Searching Authority from International Patent Application No. PCT/EP2019/051990, mailed Apr. 23, 2019.
Extended European Search Report from Application No. EP18305075.6, dated Jul. 18, 2019.

(Continued)

Primary Examiner — Wenwen Cai
(74) Attorney, Agent, or Firm — Greer, Burns & Crain, Ltd

(57) ABSTRACT

Fluorescent polymeric coating films visible in near-infrared light for coating a medical device are provided, and a method for preparing said NIR visible polymeric coating films. In particular, the fluorescent polymeric coating films visible in near-infrared light for coating a medical device are in the form of a single layer or multiple layers where said single layer or at least one of said multiple layers comprises a hydrophobic polymer, a ionic fluorescent dye and a counterion of said ionic fluorescent dye. The fluorescent dye is a near-infrared dye which belongs to the family of long-chain cyanine 7.5 derivatives, and their analogues.

11 Claims, 8 Drawing Sheets

(56) References Cited

OTHER PUBLICATIONS

Flanagan, Jr., J., Kahn, S., Menchen, S., Soper, S., Hammer, R., Functionalized Tricarbocyanine Dyes as Near-Infrared Fluorescent Probes for Biomolecules, Bioconjugate Chem., vol. 8 (5), 1997, pp. 751-756.

Gravier, J., Navarro, F., Delmas, T., Mittler, F., Couffin, A., Vinet, F., Texier, I., Lipidots: competitive organic alternative to quantum dots for in vivo fluorescence imaging, Journal of Biomedical Optics, vol. 16(9), Sep. 2011, 096013-1-096013-10.

Salon, J., Wolinska, E., Raszkiewica, A., Patonay, G., Strekowski, L., Synthesis of Benz[e]indolium Heptamethine Cyanines Containing C-Substitnents at the Central Portion of the Heptamethine Moiety, J. Heterocyclic Chem. 42, 959, Jul.-Aug. 2005, pp. 959-961.

Wang, X., Lv, J., Yao, X., Li, Y., Huang, F., Li, M., Yang, J., Ruan, X., Tang, B., Screening and investigation of a cyanine fluorescent probe for simultaneous sensing of glutathione and cysteine under single excitation, Chem. Commun, 2014, 50, pp. 15439-15442.

Notice of Reasons for Refusal received for JP Application No. 2020-562844 dated Dec. 26, 2022.

Reisch, A., et al., "Collective fluorescence switching of counterion-assembled dyes in polymer nanoparticles," Nature Communications 5, vol. 4089, 2014, 9 pages.

\* cited by examiner

PMMA only     ICG     Cy7.5-C18-TPB

Cy 7.5-C8-TPB     HA-60-TPB     HA-06-I

FLUORESCENT POLYMERIC COATING FILM FOR MEDICAL DEVICES

BACKGROUND

The present invention concerns a fluorescent polymeric coating film for medical devices and a method for coating a medical device by said fluorescent polymeric film.

During surgical operation, it is frequently difficult to localize important anatomical structure or location of pathology, because they are hidden behind other structure or they are not exposed outside of the organ. In laparoscopic surgery, it is also necessary to accurately localize the position of a surgical instrument. Thanks to its deep penetration into the tissues and high signal-to-background ratio, the near-infrared fluorescent light has been widely used in surgical operation to visualize hidden organ or tissue. Image-guided surgery using near-infrared fluorescence (NIR) could decrease the organ injury, increase the accuracy of the operation and allow carrying out a surgical operation in a region difficult to access.

Therefore, in order to be visible by surgical fluorescent imaging system during image-guided surgery using NIR, special medical tools, such as fiducials, need be marked by fluorescent dyes.

However, most of fluorescent dyes, like indocyanine green (ICG), cannot be directly used in a surgical operation, because of their easy spreading over the body which makes it difficult to control local dye spreading and dye leakage into the intraperitoneal cavity. Moreover, ICG cannot be easily conjugated with other molecules.

In the last 10 years, polymeric near-infrared fluorescent materials have been developed for coating surgical and medical instruments. Currently, the coating is nearly all based on Indocyanine green (ICG), which is the most frequently used near-infrared fluorescent dye with an approval of FDA of human usage.

For example, WO 2017/151634 describes a composition comprising a polymeric matrix and a fluorophore dye, such as rhodamine, indocyanine green or dansyl chloride for coating a medical device.

However, it is found that ICG-based polymeric coating cannot produce homogenous coating on a smooth surface, and has a limitation in stability. This means that the imaging contrast is not satisfactory and it is lost rapidly after implanting into the body.

In fact, the existing techniques for coating fiducials suffer from the following drawbacks:
1) low stability of coating leading to leakage of the dye to tissue;
2) low brightness
3) fast chemical and photo-chemical degradation (bleaching).

It is necessary to provide new NIR fluorescent materials suitable for coating medical and surgical devices and having improved brightness and in vivo stability compared to ICG-based coating materials.

SUMMARY

Against all odds, the Inventors of the present invention have observed that a particular family of near-infrared fluorescent dyes with the help of suitable counterion can be stably and homogenously immobilized in a very thin polymer layer. Said polymeric film displays a high adhesive property to smooth surface and is suitable to work as coating film on a medical device. Compared to an ICG-based coating film, the new coating film of the invention shows an improved NIR fluorescent brightness and a better in vivo stability.

Moreover, the Inventors have developed a simple and quickly carried out method for coating medical devices which allows to further increase in vivo stability of a coating film.

The first aspect of the invention concerns a coating film based on hydrophobic polymer, in particular biocompatible hydrophobic polymer, comprising a counterion and a near-infrared dye which belongs to the family of long-chain cyanine 7.5 derivatives, and their analogues.

In more detail, this aspect of the invention is to provide a fluorescent polymeric coating film visible in near-infrared light for coating a medical device, said coating film being a single layer or multiple layers of hydrophobic polymer, and at least one polymeric layer comprising an ionic fluorescent dye and its couterion, said fluorescent dye being represented by Formula I

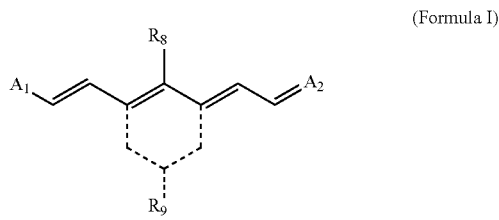

(Formula I)

wherein
$R_8$ and $R_9$ are the same or different and independently selected from a group consisting of:
an hydrogen, or
a group chosen from a (C1-C20)alkyl, a cyclo(C3-C20)alkyl, a (C2-C20)alkenyl, a (C2-C20)alkynyl, a heterocyclic group, a cyclo(C3-C20)alkenyl, a heterocyclo(C2-C20)alkenyl, an aryl, a heteroaryl, a hetero(C1-C20)alkyl, a (C1-C20)alkylaryl, or a (C1-C20)alkylheteroaryl, said group being unsubstituted or substituted by one or two substituents chosen from a (C1-C5) alkyl, an aryl, or —COOR$_{11}$, R$_{11}$ being a (C1-C20) alkyl, or
a group of formula —(E-R$_{10}$, wherein E is chosen from —O—, —S—, —Se—, —NH—, —CH$_2$—; R$_{10}$ is chosen from a (C1-C20)alkyl, a cyclo(C3-C20)alkyl, a (C2-C20)alkenyl, a (C2-C20)alkynyl, a heterocyclic group, a cyclo(C3-C20)alkenyl, a heterocyclo(C2-C20)alkenyl, an aryl, a heteroaryl, a hetero(C1-C20)alkyl, a (C1-C20)alkylaryl, a (C1-C20)alkylheteroaryl, R$_{10}$ being unsubstituted or substituted by one to three substituents chosen from a (C1-C5) alkyl, an aryl, or —COOR$_{11}$, R$_{11}$ being a (C1-C20) alkyl $A_1$ is

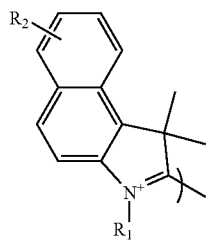

and $A_2$ is

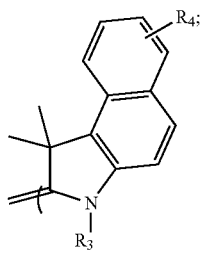

or $A_1$ is

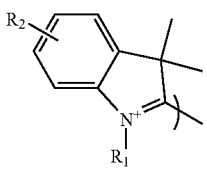

and $A_2$ is

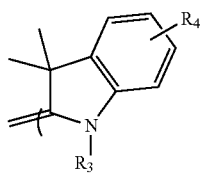

Wherein:
$R_2$ and $R_4$ are independently selected from the group consisting of hydrogen, halogen, (C1-C10)alkyl, —$OR_5$, —$NR_5R_6$, —$NO_2$, —$CF_3$, —CN, —$SR_5$, —$N_3$, —C(=O)$R_5$, —OC(=)$OR_5$, —C(=O)$NR_5R_6$, —$NR_5$C(=O)$R_6$, wherein $R_5$ and $R_6$ are independently selected from hydrogen, unsubstituted (C1-C10)alkyl, unsubstituted (C2-C10)alkenyl, unsubstituted (C2-C10)alkynyl, cyclo(C3-C10)alkyl, heterocyclic group, cyclo(C3-C10) alkenyl, heterocyclo(C2-C10)alkenyl, aryl, heteroaryl, aryl(C1-C10)alkyl, hetero(C1-C10)alkyl, (C1-C10)alkylaryl, (C1-C10)alkylheteroaryl;

$R_1$ and $R_3$ are independently selected from the group consisting of a (C1-C20)alkyl eventually substituted by a hydrophobic group, a cyclo(C3-C20) alkyl eventually substituted by a hydrophobic group, a (C2-C20)alkenyl eventually substituted by a hydrophobic group, a (C2-C20)alkynyl, a heterocyclic group eventually substituted by a hydrophobic group, a cyclo(C3-C20)alkenyl eventually substituted by a hydrophobic group, a heterocyclo(C2-C20)alkenyl eventually substituted by a hydrophobic group, an aryl eventually substituted by a hydrophobic group, a heteroaryl eventually substituted by a hydrophobic group, a hetero(C1-C20)alkyl eventually substituted by a hydrophobic group, a (C1-C20)alkylaryl eventually substituted by a hydrophobic group, a (C1-C20)alkylheteroaryl eventually substituted by a hydrophobic group, said hydrophobic group being selected from methyl, ethyl, methoxy, ethyloxy.

According to a particular embodiment, said hydrophobic polymer is chosen from poly(methyl methacrylate), poly (ethyl methacrylate), poly(propyl methacrylate), poly(butyl methacrylate), poly(methyl methacrylate-co-methacrylic acid), poly(lactide-co-glycolide), polylactic acid, polyglycolic acid, polycaprolacton, cellulose triacetate, nitrocellulose, polydimethylsiloxane, poly(ethylene terephthalate), polycarbonate, polyethylene, ethylene vinyl acetate copolymer, polyurethane, polystyrene, and copolymers thereof with poly(ethylene glycol).

Compared to ICG-based polymeric coating films, the coating films of the present invention show improved brightness of NIR fluorescence. Moreover, said coating films are also more homogeneous, stable, and have a significantly better adhesion on a smooth surface.

The term "coating film", as used herein, refers to a single layered or multiple-layered dried thin layer(s) formed after applying a solution of a polymer comprising a fluorescent dye of formula I as defined before and a counterion as mentioned hereafter.

Without being bounded by the theory, these benefits may be due to the use of a hydrophobic cyanine 7.5 derivative of formula I as defined above and of the counterions.

Indeed, above fluorescent dyes of formula I are more hydrophobic than ICG, which may help to avoid the problem of solubility encountered by ICG-based polymeric coating films.

The fluorescent dyes of formula I can be visible by a light having a wavelength of from 650 nm to 1400 nm, in particular from 700 nm to 1000 nm.

When said coating film comprises multiple polymeric layers, some polymeric layers can be devoid of a fluorescent dye and its couterion. These polymeric layers in a coating film of the invention can provide a protection or mechanical support function.

According to an embodiment of the present invention, the outermost layer is based on a biocompatible hydrophobic polymer.

Above-mentioned hydrophobic polymers are either biocompatible polymers or can be made biocompatible by conventional methods, for example by combination with poly(ethylene glycol).

The term "biocompatible hydrophobic polymer" as used herein means a hydrophobic polymer suitable to be used in living animal or human tissues or systems, and being nontoxic, noninflammatory, nonallergic, non-cancerous, without causing harm, inflammation, immune response and/or carcinogenesis in the animal or human body during the time necessary for medical operation, such as a surgery.

The employment of a biocompatible polymer allows the coating film of the Invention to be compatible with in vivo application, such as for coating a medical or surgical device.

In a particular embodiment of the invention, the fluorescent dye is represented by the formula II:

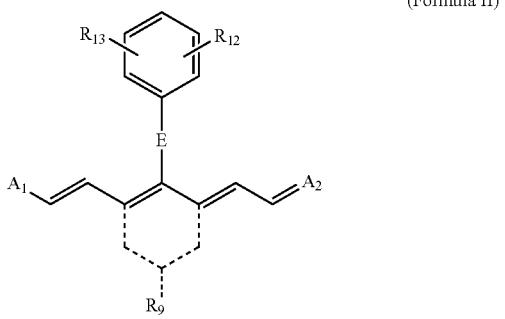

(Formula II)

Wherein:
$A_1$, $A_2$, $R_9$, and E are as defined before;
$R_{12}$ and $R_{13}$ are the same or different and independently selected from an hydrogen, an aryl, a (C1-C5) alkyl, or —$COOR_{11}$, $R_{11}$ being a (C1-C20) alkyl.

In a more particular embodiment of the invention, the fluorescent dye is represented by the formula II(a):

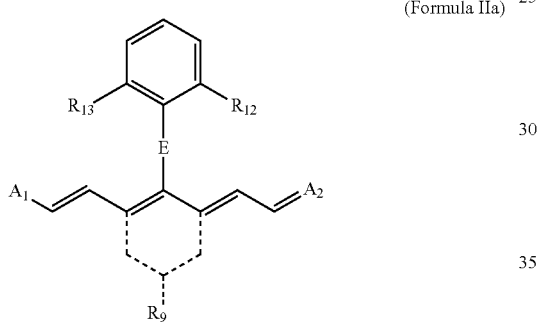

(Formula IIa)

Wherein:
$A_1$, $A_2$, $R_9$, and E are as defined before;
$R_{12}$ and $R_{13}$ are the same or different and independently selected from an aryl;
the counterion is an inorganic counterion.

In another particular embodiment of the invention is to provide a fluorescent polymeric coating film visible in near-infrared light for coating a medical device, said coating film being formed by a hydrophobic polymer, in particular a biocompatible hydrophobic polymer, a fluorescent dye and a counterion,
said fluorescent dye being represented by Formula I

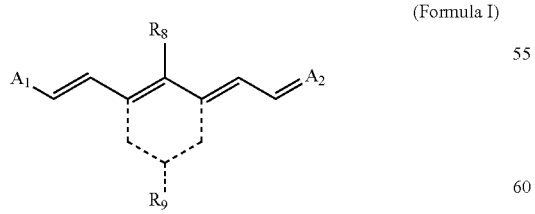

(Formula I)

wherein
$R_8$ and $R_9$ are the same or different and independently selected from the group consisting of an hydrogen, an unsubstituted (C1-C20)alkyl, an unsubstituted cyclo(C3-C20)alkyl, an unsubstituted (C2-C20)alkenyl, an unsubstituted (C2-C20)alkynyl, an unsubstituted heterocyclic group, an unsubstituted cyclo(C3-C20)alkenyl, an unsubstituted heterocyclo(C2-C20)alkenyl, an unsubstituted aryl, an unsubstituted heteroaryl, an unsubstituted hetero(C1-C20)alkyl, an unsubstituted (C1-C20)alkylaryl, an unsubstituted (C1-C20)alkylheteroaryl;

$A_1$ is

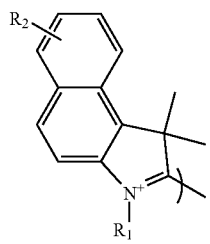

and $A_2$ is

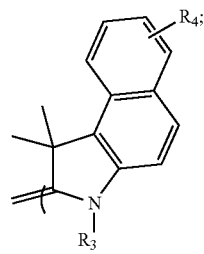

or $A_1$ is

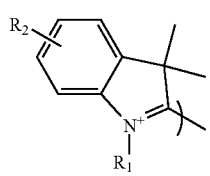

and $A_2$ is

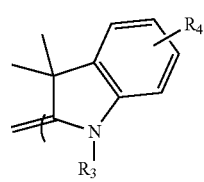

Wherein:
$R_2$ and $R_4$ are independently selected from the group consisting of hydrogen, halogen, (C1-C10)alkyl, —$OR_5$, —$NR_5R_6$, —$NO_2$, —$CF_3$, —CN, —$SR_5$, —$N_3$, —C(=O)$R_5$, —OC(=O)$R_5$, —C(=O)$NR_5R_6$, —$NR_5$C(=O)$R_6$, wherein $R_5$ and $R_6$ are independently selected from hydrogen, unsubstituted (C1-C10)alkyl, unsubstituted (C2-C10)alkenyl, unsubstituted (C2-C10)alkynyl, unsubstituted cyclo(C3-C10)alkyl, unsubstituted heterocyclic group, unsubstituted cyclo(C3-C10)alkenyl, unsubstituted heterocyclo(C2-C10)

alkenyl, unsubstituted aryl, unsubstituted heteroaryl, unsubstituted aryl(C1-C10)alkyl, unsubstituted hetero (C1-C10)alkyl, unsubstituted (C1-C10)alkylaryl, unsubstituted (C1-C10)alkylheteroaryl;

$R_1$ and $R_3$ are independently selected from the group consisting of a (C1-C20)alkyl eventually substituted by a hydrophobic group, a cyclo(C3-C20)alkyl eventually substituted by a hydrophobic group, a (C2-C20)alkenyl eventually substituted by a hydrophobic group, a (C2-C20)alkynyl eventually substituted by a hydrophobic group, a heterocyclic group eventually substituted by a hydrophobic group, a cyclo(C3-C20)alkenyl eventually substituted by a hydrophobic group, a heterocyclo(C2-C20)alkenyl eventually substituted by a hydrophobic group, an aryl eventually substituted by a hydrophobic group, a heteroaryl eventually substituted by a hydrophobic group, a hetero(C1-C20)alkyl eventually substituted by a hydrophobic group, a (C1-C20)alkylaryl eventually substituted by a hydrophobic group, a (C1-C20)alkylheteroaryl eventually substituted by a hydrophobic group, said hydrophobic group being selected from methyl, ethyl, methoxy, ethyloxy, said counterion being an inorganic counterion or a bulky organic counterion.

The presence of counterions may contribute to decrease aggregation and self-quenching of fluorescent dyes in coating film of the invention.

With regard to the present invention, the counterion is chosen from:

an inorganic counterion, an organic counterion, or a bulky organic counterion chosen from tetraphenylborate, tetrakis(pentafluorophenyl)borate, tetrakis(4-fluorophenyl)borate, tetraphenylborate, tetrakis[3,5-bis-(trifluoromethyl)phenyl]borate, tetrakis[3,5-bis-(1,1,1,3,3,3-hexafluoro-2-methoxy-2-propyl)phenyl]borate and tetrakis[perfluoro-tert-butoxy]aluminate.

The term "bulky organic counterion" as used herein means a large organic anion bearing aromatic and/or aliphatic residues.

Examples of inorganic counterion may include, without limitation, chloride, perchlorate, sulfonate, nitrate, tetrafluoroborate, hexafluorophosphate.

Examples of organic counterion may include, without limitation, acetate, formate, propionate, anions of fatty acids, benzoate, tosylate.

In order to avoid fluorescent dye aggregation and self-quenching, besides the use of an appropriate counterion, it may be also necessary to control within an appropriate range the weight of fluorescent dye compared to the polymer in a polymeric layer. Preferably, the weight of fluorescent dye in a polymeric layer is from 0.1 to 50%, particularly from 0.5 to 10%, still more particularly 1%, by weight of the hydrophobic polymer in said polymeric layer.

In the present description the term "alkyl", alone or in combination, refers to a branched or unbranched saturated hydrocarbon group having the indicated number of carbon atoms. As used herein, the term "(Cx-Cy)alkyl", wherein x and y respectively being a different positive integer, is meant to an alkyl group having from x to y number of carbon atoms. For example, the terms "(C1-C20)alkyl", "(C1-C10) alkyl", "(C8-C20)alkyl", "(C12-C18)alkyl" as used herein respectively refer to an alkyl group having from 1 to 20 carbon atoms, from 1 to 10 carbon atoms, from 8 to 20 carbon atoms or from 12 to 18 carbon atoms.

Examples of alkyl can be, but not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, n-docenyl, n-tridecyl, n-tetradecyl, n-pentadecyl, n-hexadecyl, n-heptadecyl, n-octadecyl, n-nonadecyl, n-icosyl.

The terms "hetero(C1-C10)alkyl", "hetero(C1-C20)alkyl", and "hetero(C8-C20)alkyl" respectively refer to a (C1-C10)alkyl group, a (C1-C20)alkyl group or a (C8-C20) alkyl group as defined before in which one or more carbon atoms are replaced by an oxygen, nitrogen, phosphorus or sulfur. Example of a heteroalkyl can be an alkyloxy (methoxy, ethoxy, etc), alkylmercapto (methylmercapto, ethylmercapto, erc), or an alkyloxyethyl (methoxyethyl, etc), etc.

The term "cycloalkyl" refers to a cyclic saturated carbon-based ring composed of at least three carbon atoms. The terms "cyclo(3-20)alkyl", "cyclo(3-10)alkyl" or "cyclo(8-20)alkyl" respectively refer to an cycloalkyl composed of from 3 to 20 carbon atoms, from 3 to 10 carbon atoms, or from 8 to 20 carbon atoms.

Examples of cycloalkyl groups include, but are not limited to, cyclopropyl, cyclobutyl, cyclopentyl, cyclohexyl, cycloheptyl, cyclooctyl, cyclononyl, cyclodecyl, cyclotetradecyl, cyclohexadecyl, cycloheptadecyl, cyclooctadecyl, cydononadecyl, cycloicosyl.

The term "alkenyl" as used herein, alone or in combination, refers to a branched or unbranched hydrocarbon group of the indicated number of carbon atoms having at least one carbon-carbon double bond. The terms "(C2-C20)alkenyl", "(C2-C10)alkenyl" or "(C8-C20)alkenyl" signify respectively an alkenyl group of 2 to 20 atoms, an alkenyl group of 2 to 10 carbon atoms or an alkenyl group of 8 to 20 carbon atoms.

Examples of alkenyl group are ethenyl, 1-propenyl, 2-propenyl, isopropenyl, 1-butenyl, 2-butenyl, 3-butenyl, isobutenyl, 1-pentenyl, 1-hexenyl, 1-heptenyl, 1-octenyl, 1-nonenyl, 2-nonenyl, 1-decenyl, 1-undecenyl, 1-dodecenyl, 1-tridecenyl, 1-tetradecenyl, 1-pentadecenyl, 1-hexadecenyl, 1-heptadecenyl, 1-octadecenyl, 1-nonadecenyl, 1-eicosenyl, 1,3-butadienyl, 1,4-pentadienyl.

The term "cycloalkenyl" refers to a cyclic unsaturated carbon-based ring composed of at least 3 carbon atoms and containing at least one carbon-carbon double bond. The terms "cyclo(3-20)alkenyl", "cyclo(3-10)alkenyl" and "cyclo(8-20)alkenyl" signify respectively a cycloalkenyl having 3-20 carbon atoms, a cycloalkenyl having 3-10 carbon atoms or a cyclocalkenyl having 8-20 carbon atoms.

Examples of cycloalkenyl groups include, but are not limited to, cyclopropenyl, cyclobutenyl, cyclopentenyl, cyclopentadienyl, cyclohexenyl, cyclohexadienyl, cycloheptenyl, cyclooctenyl, and the like.

The terms "heterocycloalkenyl" as used herein refers to a heterocyclic unsaturated carbon-based ring comprising at least two carbon atoms and at least one heteroatom chosen from oxygen, nitrogen, phosphorus or sulfur. The terms "heterocyclo(C2-C20)alkenyl", "heterocyclo(C2-C10)alkenyl" and "heterocyclo(C8-C20)alkenyl" respectively refer to a heterocycloalkenyl having 2-20 carbon atoms, having 2-10 carbon atoms, or having 8-20 carbon atoms.

The term "alkynyl" as used herein, alone or in combination, means a branched or unbranched hydrocarbon group of the indicated number of atoms comprising at least a triple bond between two carbon atoms. The terms "(C2-C20) alkynyl", "(C2-C10)alkynyl", or "(C8-C20)alkynyl respectively signify an alkynyl group having 2 to 20 carbon atoms, 2 to 10 carbon atoms, or 8 to 20 carbon atoms. Examples of alkynyl groups include ethynyl, propynyl, butynyl, octynyl, etc.

The term "aryl" as employed herein alone or as part of another group refers to monocyclic and bicyclic aromatic groups containing 6 to 10 carbons in the ring portion. Examples of aryl include phenyl and naphthyl.

The term "(C1-C20)alkylaryl" and "(C1-C10)alkylaryl" respectively refer to an aryl group as defined being substituted by an (C1-C20)alkyl group or an (C1-C10)alkyl group.

The term "heteroaryl" refers to an aryl group, in which one or more carbon atoms are replaced by an oxygen, a nitrogen, a phosphorus or a sulfur, for example the 4-pyridyl, 2-imidazolyl, 3-pyrazolyl and isochinolinyl group.

The term "aryl(C1-C10)alkyl" refers to a (C1-C10)alkyl as defined before being substituted by an aryl.

The terms "(C1-C20)alkylheteroaryl" and "(C1-C10)alkylheteroaryl" respectively mean a heteroaryl group as defined before being substituted by a (C1-C20)alkyl group or a (C1-C10)alkyl group.

The term "heterocyclic group" refers to a carbocyclic group, in which one or more carbon atoms are replaced by an oxygen, a nitrogen, a phosphorus, or a sulfur atom. A heterocyclic group can be a heteroaryl, a heterocycloalkyl, a heterocycloalkenyl, etc. Examples of heterocyclic group include furyl, pyrrolyl, imidazolyl, thiazolyl, isothiazolyl, pyrrolidinyl, pyridyl, quinolyl, pyrimidinyl.

The term "halogen" means fluorine, chlorine, bromine or iodine.

The terms "device" and "tool" as used herein are interchangeable.

In a preferable embodiment, when $R_2$ and/or $R_4$ of formula I, formula II, or formula IIa as described above are chosen from —$OR_5$, —$NR_5R_6$, —$SR_5$, —C(=O)$R_5$, —OC(=O)$OR_5$, —C(=O)$NR_5R_6$, —$NR_5$C(=O)$R_6$, wherein $R_5$ and $R_6$ are independently selected from unsubstituted (C1-C10)alkyl, unsubstituted (C2-C10)alkenyl, unsubstituted (C2-C10)alkynyl, unsubstituted cyclo(C3-C10)alkyl, unsubstituted cyclo(C3-C10)alkenyl, unsubstituted aryl, unsubstituted aryl(C1-C10)alkyl, unsubstituted (C1-C10)alkylaryl.

In a particular embodiment relating to the fluorescent polymeric coating film of the invention, the substituent $A_1$ of formula I as defined before is

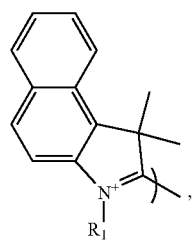

and
the substituent $A_2$ of formula I is

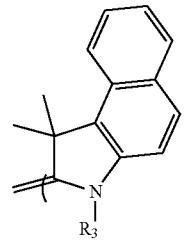

$R_1$ and $R_3$ being defined as before.

According to one embodiment of the invention, $R_1$ and $R_3$ of formula I, formula II, or formula IIa as defined before are independently selected from the group consisting of unsubstituted (C1-C20)alkyl, an unsubstituted cyclo(C3-C20)alkyl, an unsubstituted (C2-C20)alkenyl, an unsubstituted (C2-C20)alkynyl, an unsubstituted heterocyclic group, an unsubstituted cyclo(C3-C20)alkenyl, an unsubstituted heterocyclo(C2-C20)alkenyl, an unsubstituted aryl, an unsubstituted heteroaryl, an unsubstituted hetero(C1-C20)alkyl, an unsubstituted (C1-C20)alkylaryl, an unsubstituted (C1-C20)alkylheteroaryl.

According to another embodiment of the invention, each of $R_1$ and $R_3$ of formula I, formula II, or formula IIa as described above can be independently selected from an aforementioned substituent group which are substituted by a hydrophobic group.

Said hydrophobic group can be chosen from methyl, ethyl, methoxy, ethyloxy.

According to a more particular embodiment of the invention, $R_1$ and $R_3$ of formula I, formula II, or formula IIa as defined before are independently selected from the group of unsubstituted (C8-C20)alkyl, an unsubstituted cyclo(C8-C20)alkyl, an unsubstituted (C8-C20)alkenyl, an unsubstituted (C8-C20)alkynyl, an unsubstituted cyclo(C8-C20)alkenyl, an unsubstituted heterocyclo(C8-C20)alkenyl, and hetero(C8-C20)alkyl.

In a preferred embodiment of the invention, $R_1$ and $R_3$ of formula I, formula II, or formula IIa as described above are independently selected from the group of unsubstituted (C8-C20)alkyl, particularly the group of unsubstituted (C12-C18)alkyl.

In another preferred embodiment of the invention, $R_1$ and $R_3$ of formula I, formula II, or formula IIa as described above are independently selected from the group of unsubstituted (C12-C19)alkyl, (C12-C17)alkyl, or (C12-C16)alkyl, or (C12-C15)alkyl, or (C11-C19)alkyl, (C11-C18)alkyl, or (C11-C17)alkyl, or (C11-C16)alkyl, or (C11-C15)alkyl, or (C11-C14)alkyl, or (C13-C19)alkyl, or (C13-C18)alkyl, or (C13-C17)alkyl, or (C13-C16)alkyl, or (C14-C19)alkyl, or (C14-C18)alkyl, or (C14-C17)alkyl, or (C15-C19)alkyl, or (C15-C18)alkyl.

More preferably, $R_1$ and $R_3$ of formula I, formula II, or formula IIa as described above are independently selected from n-docenyl, n-tridecyl, n-tetradecyl, n-pentadecyl, n-hexadecyl, n-heptadecyl, n-octadecyl, n-nonadecyl, or n-icosyl.

A particular embodiment of the present invention concerns a fluorescent polymeric coating film, wherein the fluorescent dye is of Formula Ia (Formula Ia)

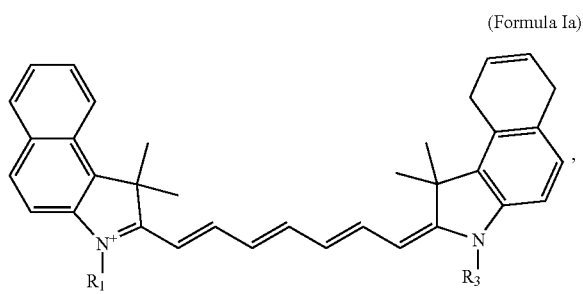

or (Formula Ib)

(Formula Ib)

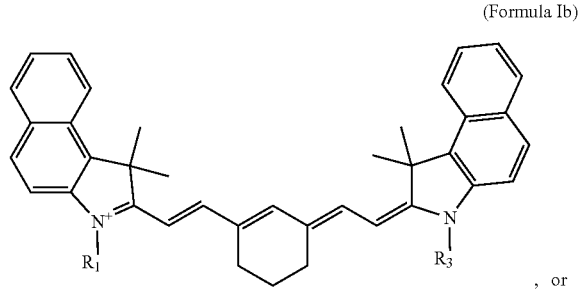

, or (Formula IIb)

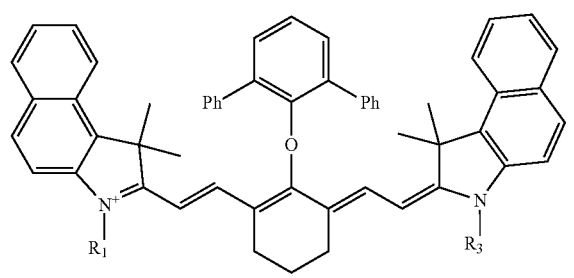

$R_1$ and $R_3$ being independently selected from the group of unsubstituted (C8-C20)alkyl, particularly the group of unsubstituted (C12-C18)alkyl.

A more particular embodiment of the present invention is related to a fluorescent coating film wherein the fluorescent dye is

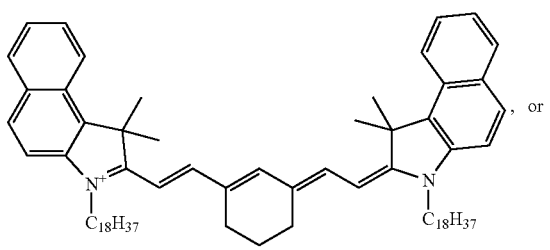

, or

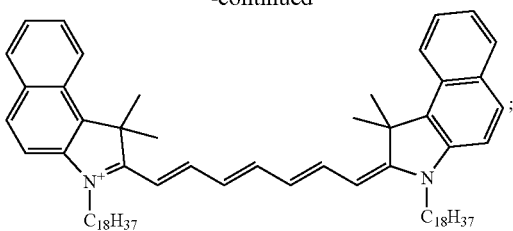

;

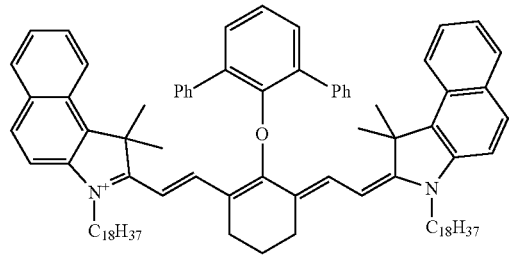

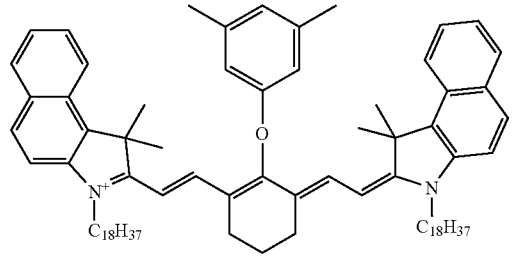

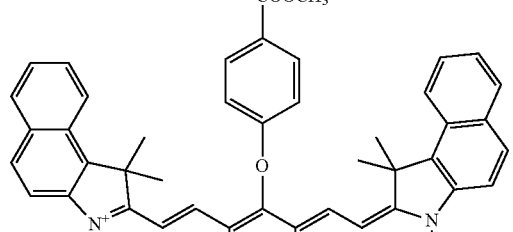

.

The polymer contained in the coating film of the invention is also preferably non-biodegradable to avoid the spreading of fluorescent dyes in the tissues.

The term "biodegradable" as used herein refers to the propriety of a polymer which can be degraded into a low molecular weight material through a degradation process such as a hydrolytic reaction or enzymatic reaction during the metabolism in the animal or human body.

In a preferred embodiment of the present invention, said polymer is chosen from poly(D,L-lactide-co-glycolide), poly(methyl methacrylate) and polycaprolactone.

In a more preferred embodiment of the present invention, said polymer is chosen from poly(methyl methacrylate) and polycaprolactone.

Owing to biocompatibility of the coating film of the invention, it is particularly suitable to be applied to medical or surgical devices, such as a surgical packing, fiducial marker, a surgical tap, a needle, a surgical retractor, a clip, a surgical thread, a staple, a knife, a safety pin, a scissor, a clamp, a scalpel, a hemostat, a tweezer, a forcep, a suction tip, a gauze, a cottonoid, a sponge, a catheter, a stainless steel wire, a surgical site marker, a stent, a pacemaker, a nerve stimulator, a drug delivery system, a port-a-cath, a magnetic anastomosis system, an intravascular embolization device, a mechanical linear stapler, a mechanical circular stapler, a drug-delivery implant, a piezoelectric implant, a diagnostic video-capsule, a magnetic tracking capsule.

For example, a surgical marker or a catheter coated by a coating film of the present invention is particularly useful in identification of tumors or vulnerable anatomical structures.

The intraluminal instruments or implants coated by a coating film of the present invention can be visualized by conventional surgical fluorescent imaging system or by Near-Infrared spectroscopy, which makes it easy to identify said instruments or implants during image-guided surgery, even though when they are hidden behind a tissue or an organ.

The fluorescent polymeric film of the present invention is visible in near-infrared light having a wavelength of from 650 nm to 1400 nm, in particular from 700 nm to 1000 nm.

The fluorescent polymeric film of the present invention can further comprise, in one or several polymeric layers, one or several additives which can be a polymer or a small organic molecule having function to improve mechanical properties or biocompatibility of coating film.

A fluorescent polymeric coating film visible in near-infrared light can also be used as a fluorescent marker of a biological tissue, especially a human or animal tissue, such as an organ, during a surgery.

Said coating film is a single layer or multiple layers of hydrophobic polymer, and at least one polymeric layer comprising a fluorescent dye of formula I, I(a), I(b), II, II(a) or II(b) as described above and an ionic counterion as described above.

Preferably, at least the outermost polymeric layer of the coating film is based on a biocompatible hydrophobic polymer.

A second aspect of the present invention concerns a method for coating a medical device by a fluorescent polymeric coating film as described before.

Said method is carried out by employment of a solution of hydrophobic polymer comprising an aforementioned ionic fluorescent dye of formula I, a counterion and an organic volatile solvent.

Said method comprises following steps:
(i) contacting said medical device with a solution comprising one or several solvents, a hydrophobic polymer, a fluorescent dye and a counterion,
said hydrophobic polymer being chosen from poly(methyl methacrylate), poly(ethyl methacrylate), poly(propyl methacrylate), poly(butyl methacrylate), poly(methyl methacrylate-co-methacrylic acid), poly(lactide-co-glycolide), polylactic acid, polyglycolic acid, polycaprolacton, cellulose triacetate, nitrocellulose, polydimethylsiloxane, poly(ethylene terephthalate), polycarbonate, polyethylene, ethylene vinyl acetate copolymer, polyurethane, polystyrene, and copolymers thereof with poly(ethylene glycol); said fluorescent dye being represented by Formula I

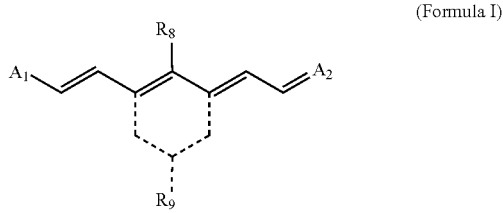

(Formula I)

wherein:

$R_8$ and $R_9$ are the same or different and independently selected from the group consisting of:

an hydrogen, a group chosen from a (C1-C20)alkyl, a cyclo(C3-C20)alkyl, a (C2-C20)alkenyl, a (C2-C20)alkynyl, a heterocyclic group, a cyclo(C3-C20)alkenyl, a heterocyclo(C2-C20)alkenyl, an aryl, a heteroaryl, a hetero(C1-C20)alkyl, a (C1-C20)alkylaryl, or a (C1 C20)alkylheteroaryl, said group being unsubstituted or substituted by one or two substituents chosen from a (C1-C5) alkyl, an aryl, or —COOR$_{11}$, R$_{11}$ being a (C1-C20) alkyl, or a group of formula ╋E-R$_{10}$, wherein E is chosen from —O—, —S—, —Se—, —NH—, —CH$_2$—; R$_{10}$ is chosen from a (C1-C20)alkyl, a cyclo(C3-C20)alkyl, a (C2-C20)alkenyl, a (C2-C20)alkynyl, a heterocyclic group, a cyclo(C3-C20)alkenyl, a heterocyclo(C2-C20)alkenyl, an aryl, a heteroaryl, a hetero(C1-C20)alkyl, a (C1-C20)alkylaryl, a (C1-C20)alkylheteroaryl, R$_{10}$ being unsubstituted or substituted by one or two substituents chosen from a (C1-C5) alkyl, an aryl, or —COOR$_{11}$, R$_1$ being a (C1-C20) alkyl A$_1$ is

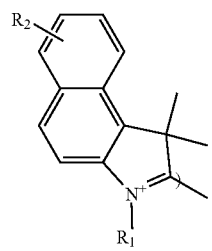

and A$_2$ is

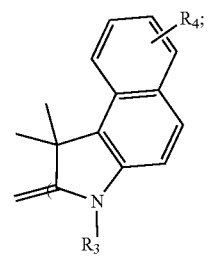

or A$_1$ is

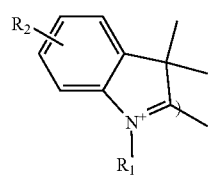

and $A_2$ is

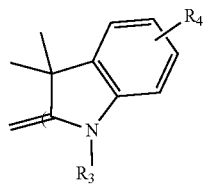

Wherein:
  $R_2$ and $R_4$ are independently selected from the group consisting of hydrogen, halogen, (C1-C10)alkyl, —$OR_5$, —$NR_5R_6$, —$NO_2$, —$CF_3$, —CN, —$SR_5$, —$N_3$, —C(=O)$R_5$, —OC(=)$OR_5$, —C(=O)$NR_5R_6$, —$NR_5$C(=O)$R_6$, wherein $R_5$ and $R_6$ are independently selected from hydrogen, unsubstituted (C1-C10)alkyl, unsubstituted (C2-C10)alkenyl, unsubstituted (C2-C10)alkynyl, cyclo(C3-C10)alkyl, heterocyclic group, cyclo(C3-C10)alkenyl, heterocyclo(C2-C10)alkenyl, aryl, heteroaryl, aryl(C1-C10)alkyl, hetero(C1-C10)alkyl, (C1-C10)alkylaryl, (C1-C10)alkylheteroaryl;
  $R_1$ and $R_3$ are independently selected from the group consisting of a (C1-C20)alkyl eventually substituted by a hydrophobic group, a cyclo(C3-C20)alkyl eventually substituted by an hydrophobic group, a (C2-C20)alkenyl eventually substituted by a hydrophobic group, a (C2-C20)alkynyl, a heterocyclic group eventually substituted by a hydrophobic group, a cyclo(C3-C20)alkenyl eventually substituted by a hydrophobic group, a heterocyclo(C2-C20)alkenyl eventually substituted by a hydrophobic group, an aryl eventually substituted by a hydrophobic group, a heteroaryl eventually substituted by a hydrophobic group, a hetero(C1-C20)alkyl eventually substituted by a hydrophobic group, a (C1-C20)alkylaryl eventually substituted by a hydrophobic group, a (C1-C20)alkylheteroaryl eventually substituted by a hydrophobic group, said hydrophobic group being selected from methyl, ethyl, methoxy, ethyloxy;
  said counterion being an inorganic counterion, or an organic counterion or a bulky organic counterion;
(ii) Evaporating the solvent in said solution to form one polymeric layer comprising a fluorescent dye and a counterion on said medical device.

According to a particular embodiment of the method of coating of the present invention, the fluorescent dye is represented by Formula I

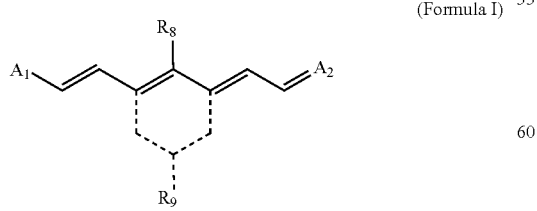

(Formula I)

wherein
  $R_8$ and $R_9$ are the same or different and independently selected from the group consisting of an hydrogen, an unsubstituted (C1-C20)alkyl, an unsubstituted cyclo(C3-C20)alkyl, an unsubstituted (C2-C20)alkenyl, an unsubstituted (C2-C20)alkynyl, an unsubstituted heterocyclic group, an unsubstituted cyclo(C3-C20)alkenyl, an unsubstituted heterocyclo(C2-C20)alkenyl, an unsubstituted aryl, an unsubstituted heteroaryl, an unsubstituted hetero(C1-C20)alkyl, an unsubstituted (C1-C20)alkylaryl, an unsubstituted (C1-C20)alkylheteroaryl;
$A_1$ is

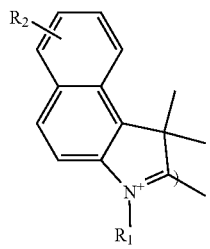

and $A_2$ is

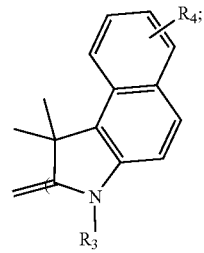

or $A_1$ is

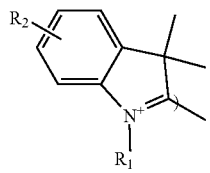

and $A_2$ is

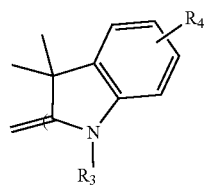

Wherein:
  $R_2$ and $R_4$ are independently selected from the group consisting of hydrogen, halogen, (C1-C10)alkyl, —$OR_5$, —$NR_5R_6$, —$NO_2$, —$CF_3$, —CN, —$SR_5$, —$N_3$, —C(=O)$R_5$, —OC(=)$OR_5$, —C(=O)$NR_5R_6$, —$NR_5$C(=O)$R_6$, wherein $R_5$ and $R_6$ are independently selected from hydrogen, unsubstituted (C1-C10)alkyl, unsubstituted (C2-C10)alkenyl, unsubstituted (C2-C10)alkynyl, cyclo(C3-C10)alkyl, heterocyclic group, cyclo(C3-C10) alkenyl, heterocyclo(C2-C10)alkenyl, aryl, heteroaryl, aryl(C1-C10)alkyl, hetero(C1-C10)alkyl, (C1-C10)alkylaryl, (C1-C10)alkylheteroaryl;

$R_1$ and $R_3$ are independently selected from the group consisting of a (C1-C20)alkyl eventually substituted by an hydrophobic group, a cyclo(C3-C20) alkyl eventually substituted by an hydrophobic group, a (C2-C20)alkenyl eventually substituted by a hydrophobic group, a (C2-C20)alkynyl, a heterocyclic group eventually substituted by a hydrophobic group, a cyclo(C3-C20)alkenyl eventually substituted by a hydrophobic group, a heterocyclo(C2-C20)alkenyl eventually substituted by a hydrophobic group, an aryl eventually substituted by a hydrophobic group, a heteroaryl eventually substituted by a hydrophobic group, a hetero(C1-C20)alkyl eventually substituted by a hydrophobic group, a (C1-C20)alkylaryl eventually substituted by a hydrophobic group, a (C1-C20)alkylheteroaryl eventually substituted by a hydrophobic group, said hydrophobic group being selected from methyl, ethyl, methoxy, ethyloxy;

said counterion being an inorganic counterion or a bulky organic counterion chosen from tetrakis(pentafluorophenyl)borate, tetrakis(4-fluorophenyl)borate, tetraphenylborate.

Solvent used in the solution of step (i) can be an organic solvent, in particular chosen from acetonitrile, acetone, dioxane, ethyl acetate, propyl acetate, butyl acetate, amyl acetate, tetrahydrofuran, diethyl ether, 1,2-dimethoxyethane, 1,2-dioxane, dichloromethane, chloroform, petroleum ether, toluene, o-xylene, m-xylene, p-xylene.

Particularly, the concentration of the hydrophobic polymer in above solution is from 1 to 100 mg/ml, preferably 30 mg/ml of solution and the weight of fluorescent dye in a polymeric layer is from 0.1 to 50%, particularly from 0.5 to 10%, still more particularly 1%, by weight of the hydrophobic polymer in said polymeric layer.

The step (i) of above method can be done by simple immersion of the tool to be coated inside the solution. The step (ii) of above method can be a step of drying in air. The time of drying for evaporating the solvent can be for example 30 minutes. This step is preferably carried out in dark.

According to an advantageous embodiment, when said coating film is multi-layered, said method further comprises step (iii) and step (iv) after the step (ii):

(iii) Contacting coated medical device obtained in step (ii) with a solution comprising one or several solvents and a hydrophobic polymer and eventually devoid of any fluorescent dye;

(iv) Evaporating the solvent in said solution to produce a polymeric layer on said medical device.

The application of steps (iii) and (iv) produces a protective film at the outside surface of the coating film containing the fluorescent dyes and can further reduce the risk of fluorescent dyes spreading in animal or human body. The step (iv) can be carried out in dark during 24 hours.

Immersion and drying steps can be alternately repeated several times to increase the performance of the tool. Each time, the step (i) is repeated when the solvent is completed evaporated and the forming coating film is completed dried.

According to an embodiment of the invention, the steps (i) and (ii) as described before are repeated from 1 to 50 times, preferably 1 to 20 times.

According to another embodiment of the invention, the steps (iii) and (iv) as described before are repeated from 1 to 20 times.

In a preferred embodiment of the method of the invention, a repetition of steps (i) and (ii) is firstly carried out to coat a medical device by a coating film described before, and after complete drying of said coating film, a repetition of steps (iii) and (iv) is then employed to yield a protective outside film.

Aforementioned method is suitable for coating a medical device chosen from a surgical packing, fiducial marker, a surgical tap, a needle, a surgical retractor, a clip, a surgical thread, a staple, a knife, a safety pin, a scissor, a clamp, a scalpel, a hemostat, a tweezer, a forcep, a suction tip, a gauze, a cottonoid, a sponge, a catheter, a stainless steel wire, a surgical site marker, a stent, a pacemaker, a nerve stimulator, a drug delivery system, a port-a-cath, a magnetic anastomosis system, an intravascular embolization device, a mechanical linear stapler, a mechanical circular stapler, a drug-delivery implant, a piezoelectric implant, a diagnostic video-capsule, a magnetic tracking capsule.

According to a particular embodiment, the method of the invention uses a fluorescent dye of formula I, wherein A1 is

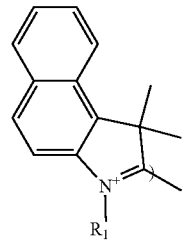

and A2 is

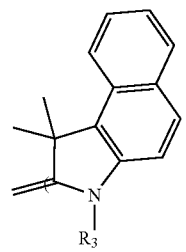

$R_1$ and $R_3$ being as defined before.

In a preferred embodiment, the method of the invention uses a fluorescent dye of formula I, wherein $R_1$ and $R_3$ are independently selected from the group of unsubstituted (C8-C20)alkyl, particularly the group of unsubstituted (C12-C18)alkyl.

More preferably, the fluorescent dye used in the method of the present invention is

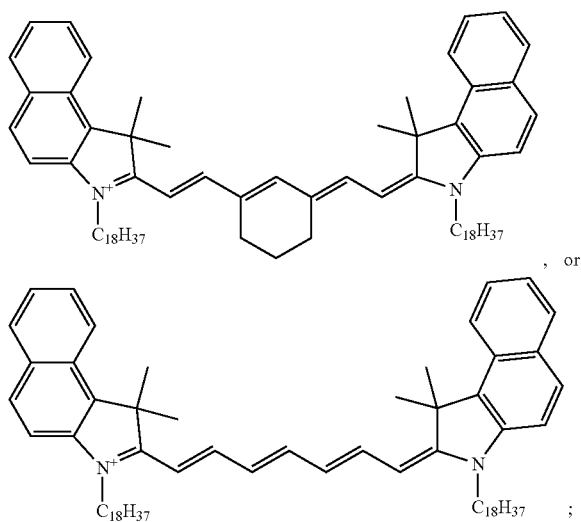

, or and the counterion used in the method is tetraphenylborate.

Another aspect of the present invention is to provide a method for visualizing a medical device during image-guided surgery, said method comprising:

Coating said medical device by an aforementioned coating film,

Visualizing said medical device by a fluorescent image system which detects near-infrared fluorescence.

The present invention is described in more detail hereinafter by the figures and the examples.

BRIEF DESCRIPTION OF THE DRAWINGS

FIG. 10 (B) shows emission intensity values obtained from the images of the thin films containing different types of fluorescent dyes and polymers.

DETAILED DESCRIPTION

Figure 1:
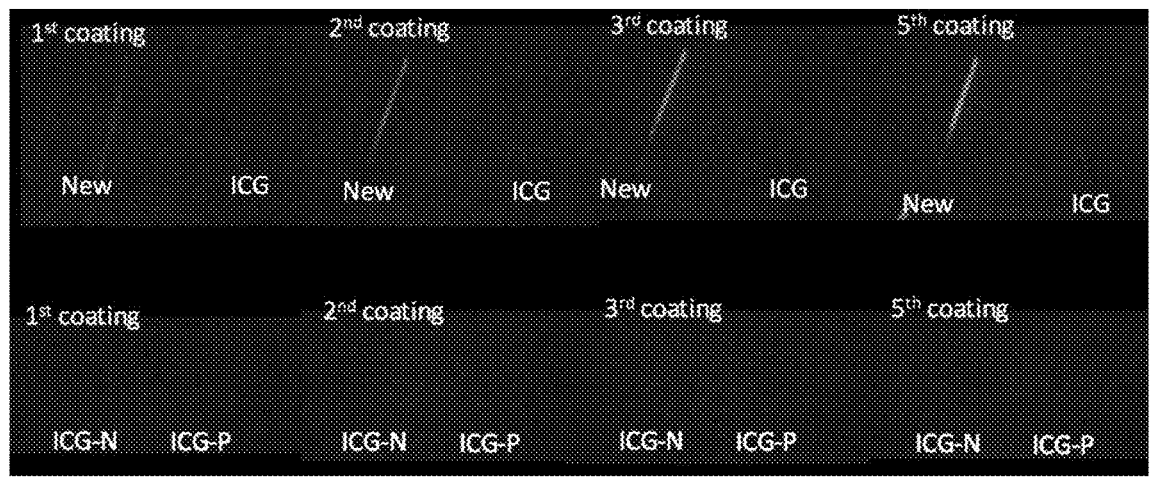
FIG. 1 concerns photos of coated stainless steel wires taken by a fluorescent image system. These wires are respectively coated 1, 2, 3 or 5 times by a coating film of the invention (New, Cy7.5-C18-TPB-based coating) or by three different ICG-based coating films (ICG, ICG salt with tetraphenyl phosphonium counterion (ICG-P), ICG salt with tetrabutyl ammonium counterion (ICG-N)).

1. Materials and Methods 1.1 Synthesis of Cy7.5-C18-TPB

Fluorescent dye Cy7.5-C18-TPB of structure before:

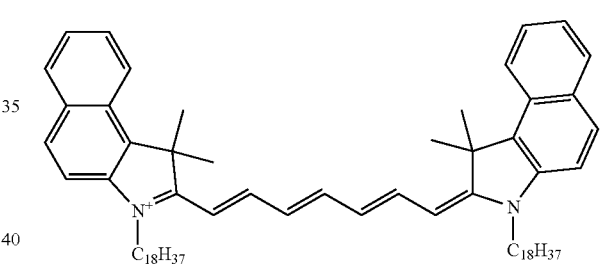

is synthesized according to protocol below and summarized in schema 1(a) of FIG. 8.

1.1.2-trimethyl-3-octadecyl-1H-benzo[e]indol-3-ium iodide 250 mL round-bottom flask equipped with magnetic stirring bar was charged with 1,1,2-Trimethylbenz[e]indole (1 eq., 6.88 g, 32.9 mmol) and 1-iodooctadecane (2 eq., 25 g, 65.7 mmol), 100 mL of 2-butanone was added subsequently. Reaction mixture was refluxed for 24 h, then cooled down to r.t. Reaction mixture was cooled down to r.t., diethyl ether was added and formed solid part was filtered off and washed with 100 mL of diethyl ether. Obtained crystals of crude product were redissolved in DCM and precipitated back while by adding diethyl ether, afterwards filtered and washed with diethyl ether. Product was obtained as slightly green crystals in 76% yield (14.73 g).

$^1$H NMR (400 MHz, CDCl$_3$) δ 8.10 (d, J=8.7 Hz, 1H), 8.08 (dd, J=8.0, 1.1 Hz, 1H), 8.04 (dd, J=8.2, 1.3 Hz, 1H), 7.76 (d, J=8.9 Hz, 1H), 7.72 (ddd, J=8.3, 6.9, 1.4 Hz, 1H), 7.65 (ddd, J=8.1, 6.9, 1.2 Hz, 1H), 4.78 (t, J=7.7 Hz, 2H), 3.19 (s, 3H), 1.97 (p, J=7.8 Hz, 2H), 1.87 (s, 6H), 1.52-1.41 (m, 2H), 1.40-1.30 (m, 2H), 1.28-1.19 (m, 26H), 0.85 (t, J=7.0 Hz, 3H).

$^{13}$C NMR (100 MHz, CDCl$_3$) δ 195.25, 138.34, 137.29, 133.82, 131.56, 130.17, 128.77, 127.97, 127.74, 122.96, 112.59, 56.04, 50.56, 32.00, 29.77, 29.76, 29.73, 29.70, 29.65, 29.55, 29.43, 29.41, 29.24, 28.26, 26.92, 22.85, 22.76, 17.03, 14.18.

HRMS (m/z): [M]$^+$ calculated for C$_{33}$H$_{52}$N 462.40943; found 462.40854.

Dioctadecylcyanine 7.5 Chloride:

1,1,2-trimethyl-3-octadecyl-1H-benzo[e]indol-3-ium iodide (1) (2.2 eq., 1029 mg, 1.75 mmol) and glutaconaldehydedianil hydrochloride (1 eq., 226 mg, 0.794 mmol) were mixed in 10 ml of pyridine, afterwards Ac$_2$O (13.4 eq., 1087 mg, 1 mL, 10.6 mmol) was added and the reaction mixture was heated to 60° C. while stirring and left for 3 h. After reaction was finished, solvents were evaporated at vacuum, and the crude product was dissolved in DCM, washed with 0.1 N HCl (3 times), brine and water. DCM layer was dried over Na$_2$SO$_4$, the solvent was evaporated and the product was purified by column chromatography on silica (gradient DCM/MeOH 99/1-95/5). Product was obtained as a green solid (926 mg, 0.906 mmol, 52%)

$^1$H NMR (400 MHz, CDCl$_3$): δ 8.16 (d, 1=8 Hz, 2H), 8.06 (t, J=12 Hz, 2H), 7.97 (bs, 1H), 7.92 (d, J=8 Hz, 4H), 7.61 (t, J=7 Hz, 2H), 7.46 (t, J=7 Hz, 2H), 7.35 (d, J=9 Hz, 2H), 6.67 (t, J=12 Hz, 2H), 6.25 (d, J=12 Hz, 2H), 4.14 (bs, 4H), 2.04 (s, 12H), 1.87 (m, J=7 Hz, 4H), 1.49 (m, J=7 Hz, 4H), 1.39 (m, J=7 Hz, 4H), 1.26 (bs, 52H), 0.88 (t, J=7 Hz, 6H)

$^{13}$C NMR (100 MHz, CDCl$_3$): δ 173.07, 157.04, 151.02, 139.74, 133.98, 131.83, 130.59, 130.09, 128.41, 127.87, 126.27, 125.06, 122.47, 110.56, 103.39, 51.155, 44.76, 32.06, 29.842, 29.807, 29.76, 29.72, 29.60, 29.53, 29.50, 27.86, 27.14, 22.82, 14.26

HRMS (m/z): [M]$^+$ calculated. for C$_{71}$H$_{105}$N$_2^+$ 985.8272; found 985.8290.

Dioctadecylcyanine 7.5 tetraphenylborate (Cy7.5-C18-TPB):

Dioctadecylcyanine 7.5 chloride (1 eq., 200 mg, 0.18 mmol) was dissolved in 5 mL of DCM, sodium tetraphenylborate (3 eq., 184 mg, 0.539 mmol) was added and the dispersion was sonicated for 5 min. TLC control has shown full conversion. Afterwards, the mixture was purified on a silica column, eluent DCM/MeOH 95/5 (product goes almost with front). Dioctadecylcyanine 7.5 tetraphenylborate (218 mg, 0.167 mmol, 93%) was obtained as green viscous oil and used without further characterisation.

Synthesis of CY 7.5-C8-I:

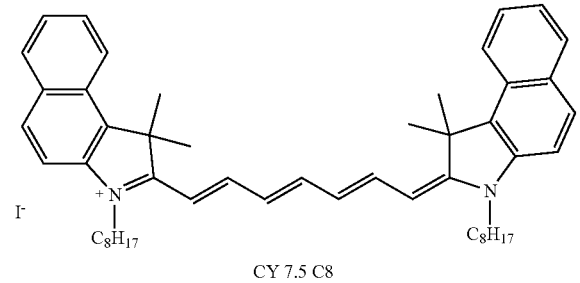

CY 7.5 C8

CY 7.5 C8 was synthesized by following our previous method. 1,1,2-trimethyl-3-octyl-1H-benzo[e]indol-3-ium iodide (2 equiv.), glutaconaldehydedianil hydrochloride (1 equiv.) were mixed in pyridine. Acetic anhydride (13.4 equiv.) was added and stirred at 60° C. for 3 hours. Reaction was monitored by TLC. Upon completion, solvent was evaporated under vacuum, dissolved in DCM and washed with 0.1 N HCl for 3 times. Organic mass was further washed with water and brine, dried on magnesium sulphate and purified by silica gel column chromatography using DCM and Methanol. Yield 60% $^1$H NMR (CD$_3$OD, 500 MHz) δ 0.85-0.89 (t, 6H), 1.26-1.27 (m, 12H), 1.37*1.49 (m, 6H), 1.70-1.74 (m, 1H), 1.79-1.85 (m, 2H), 1.96 (s, 7H), 1.99 (s, 2H), 2.11 (s, 6H), 2.16 (s, 2H), 3.81-3.85 (m, 1H), 4.15-4.19 (m, 2H), 6.29-6.32 (d, 1H, J=13.68 Hz), 6.56-6.63 (t, 1H, J=12.55 Hz), 7.05-7.08 (t, 2H, J=7.40 Hz), 7.26-7.30 (t, 5H, J=8.53), 7.43-7.47 (t, 1H, J=7.91 Hz), 7.52-7.54 (d, 5H, J=9.79 Hz), 7.59-7.63 (t, 1H, J=6.90 Hz), 7.81-7.86 (m, 1H), 7.95-8.04 (m, 2H), 8.19-8.21 (d, 1H, J=8.53 Hz). BRMS (ES+), m/z [M+H] 705.5210.

Synthetic Routes for Other Cyanine 7.5 Derivatives.

Substituted cyclic analogues of cyanine 7.5 dye (scheme 1b of FIG. 8) were synthesized in five steps. Indolinium salts with C8 or C18 alkyl chains were synthesized by the condensation of trimethyl benzindole with alkyl iodide. Formylation of cyclohexanone followed by condensation with aniline in the presence of HCl resulted in the cyclic inner salt (b). Condensation of inner salt (b) and indolinium salt in the presence of sodium acetate resulted in a key intermediate cyclic chloro-cyanine. Substitution of -chloro with different phenol derivatives followed by the counter ion exchange with tetraphenyl borate resulted in a series of cyanine derivatives.

Figure 8:
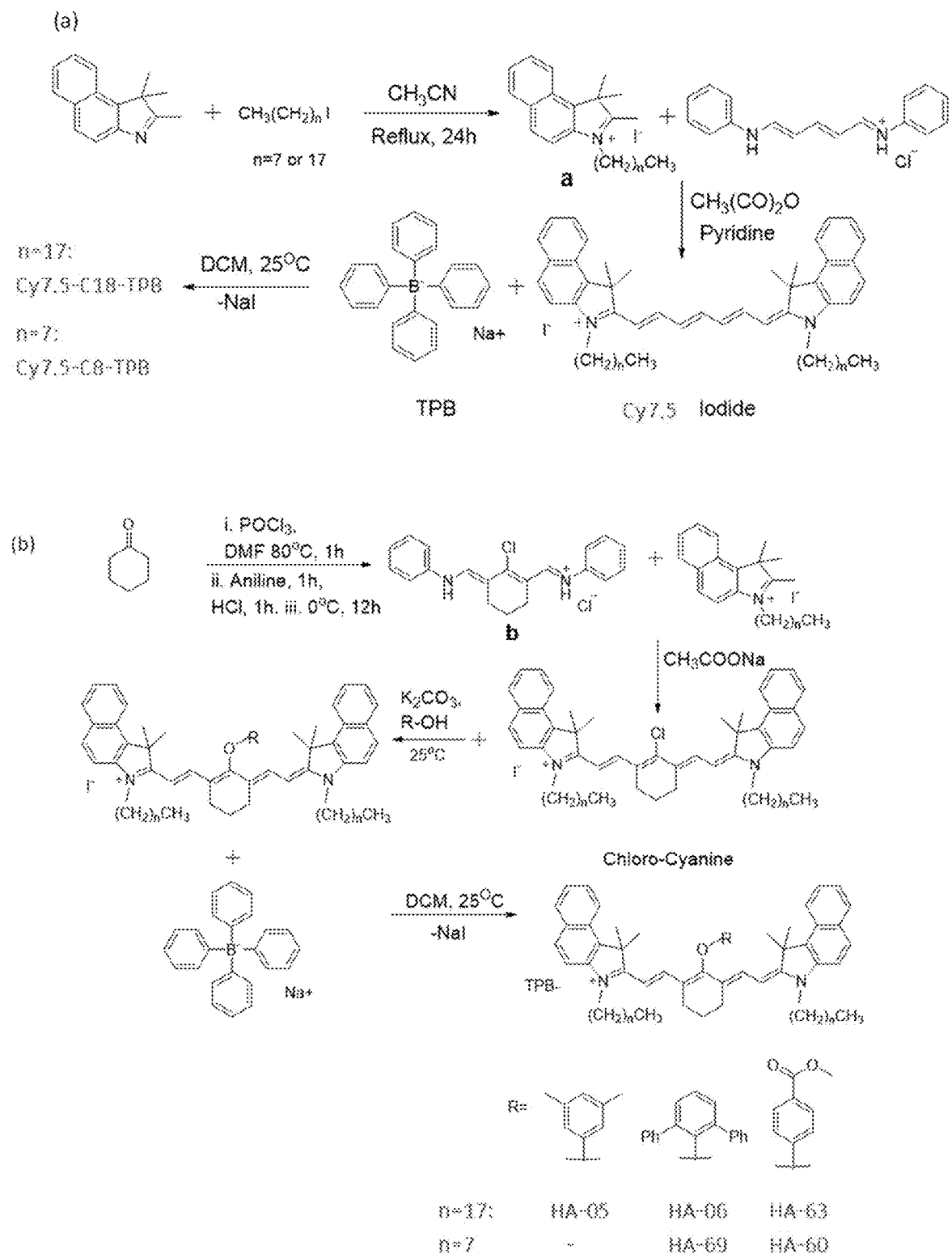
FIG. 8 shows synthetic protocols for CY7.5 dye and its derivatives of formula I.
Figure 8:
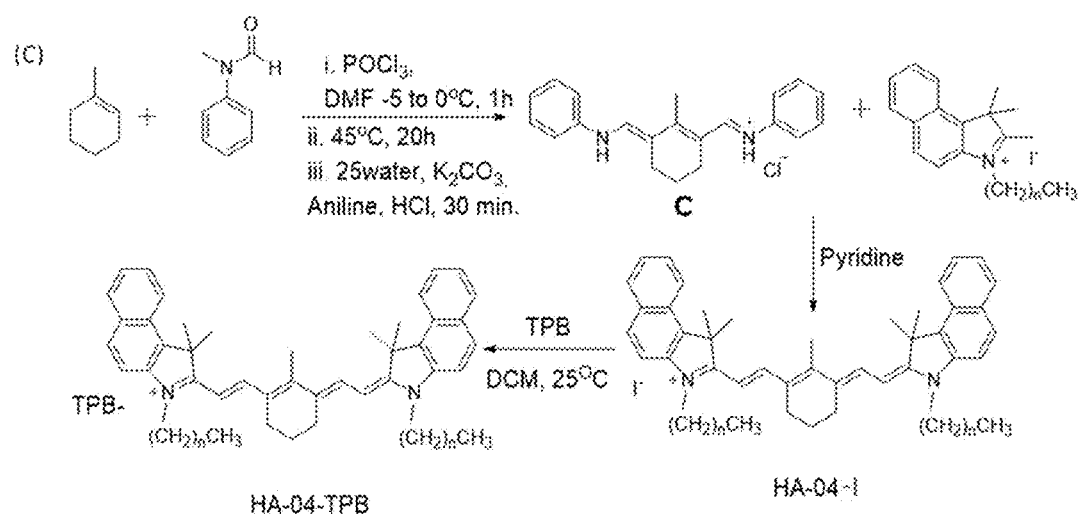

Cyclic cyanine dye having methyl group on the central cyclic ring (HA-04-I) was prepared by following the different route (scheme 1c of FIG. 8). Inner salt was prepared from 1-methylcyclohexene in the presence of N-methyl-N-phenyl formamide and POCl$_3$. Condensation of inner salt with indolinium salt in the presence of pyridine resulted in the final compound.

Synthesis of Inner Salt (b):

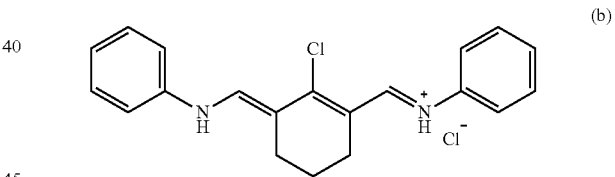

This compound was prepared by following the literature method (*Bioconjugate Chem.* 1997, 8, 751-756; Chem. Commun., 2014, 50, 15439-15442). Yield 57%

$^1$H NMR (DMSO d$_6$, 400 MHz) δ 1.84 (s, 2H), 2.74 (s, 4H), 7.20-7.26 (m, 2H), 7.41-7.46 (m, 6H), 7.55-7.57 (d, 4H, 3=7.91 Hz), 7.70-7.72 (d, 1H, J=7.71 Hz), 8.68 (s, 2H).

As what is shown in schema 1b of FIG. 8, chloro-cyanine (10 mg, 0.0084 mmol, 1 equiv.) was dissolved in dry DMF (2 ml) at 25° C. In a separate round bottom flask, 2,6-dipehenylphenol (10.34 mg, 0.0420 mmol, 5 equiv.) was dissolved in dry DMF (2 ml) and dry K$_2$CO$_3$ (2.32 mg, 0.0168 mmol 2 equiv.) was added to it and the solution was stirred for 10-15 minutes. It was carefully filtered to get rid of the unreacted K$_2$CO$_3$ and the filtrate was slowly added to the solution of chloro-cyanine. The reaction mass was stirred at 25° C. for 30 minutes. The reaction was monitored by UV-Vis spectroscopy characterized by the disappearance of the absorption band at around 820 nm (corresponds to chloro-cyanine) and the formation of a new absorption band at shorter wavelength region. Upon completion, the reaction was quenched with solid CO$_2$ and concentrated under vacuum to remove the DMF. The reaction mass was redissolved in dichloromethane and purified by silica gel column chromatography using dichloromethane/methanol as eluents.

Characterisation of Substituted Cyanine 7.5 Dye

Six derivatives of cyanine 7.5 dye of formula (I) of the present invention: HA-06, HA-04, HA-05, HA-60, HA-63, HA-69, as iodide or tetraphenylborate (TB) salts, were synthesised according to the protocol described above.

HA-06-I:

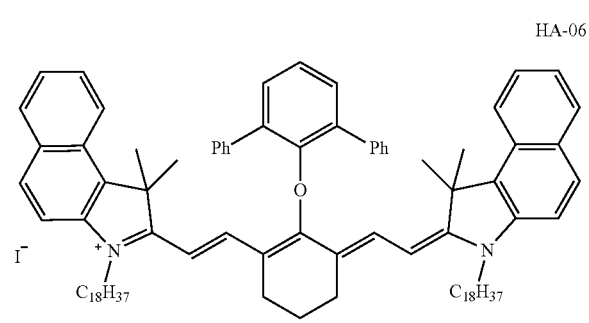

HA-06

The title compound (68%, green solid) was prepared from 2,6-diphenylphenol according to the general protocol S1. $^1$H NMR (CD$_3$OD, 400 MHz) δ 0.84-0.87 (t, 6H), 1.24 (s, 59H), 1.39-1.47 (m, 9H), 1.71 (s, 10H), 1.84-1.88 (t, 3H), 2.03 (s, 2H), 2.15-2.18 (t, 4H), 4.16-4.20 (t, 4H), 4.60 (s, 1H), 5.96-5.99 (d, 2H J=14.05 Hz), 7.30-7.34 (t, 1H, J=7.40 Hz), 7.37-7.47 (m, 9H), 7.49-7.64 (m, 8H), 7.95-7.99 (t, 4H, J=8.53 Hz), 8.08 (s, 1H), 8.12-8.15 (t, 3H, J=3H) BRMS (ES+), m/z [M+H] 1270.9522.

HA-04-I:

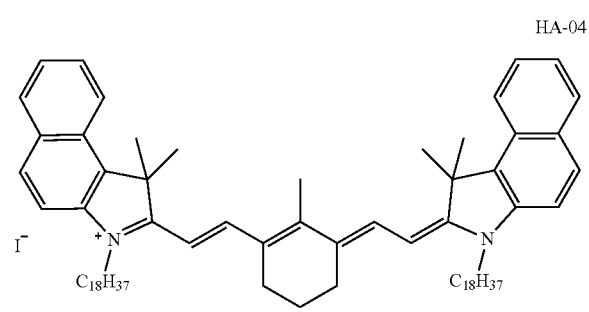

HA-04

$^1$H NMR (CD$_3$OD, 400 MHz) δ 0.85-0.88 (t, 6H), 1.26 (s, 51H), 1.44-1.47 (m, 4H), 1.50-1.53 (m, 3H), 1.89-1.93 (m, 4H), 1.96-1.98 (m, 2H), 2.04 (s, 12H), 2.56 (s, 3H), 2.64-2.67 (t, 4H), 4.25-4.28 (t, 4H), 4.61 (s, 1H), 6.28-6.30 (2H, d, J=13.73), 7.47-7.50 (t, 2H, J=7.17 Hz) 7.58-7.60 (2H, J=8.85 Hz), 7.63-7.66 (2H, J=7.17 Hz), 7.99-8.03 (q, 4H), 8.25-8.27 (d, 2H, J=8.54 Hz), 8.29-8.31 (d, 2H, J=13.29 Hz). BRMS (ES+), m/z [M+H] 1039.8734.

HA-05-I:

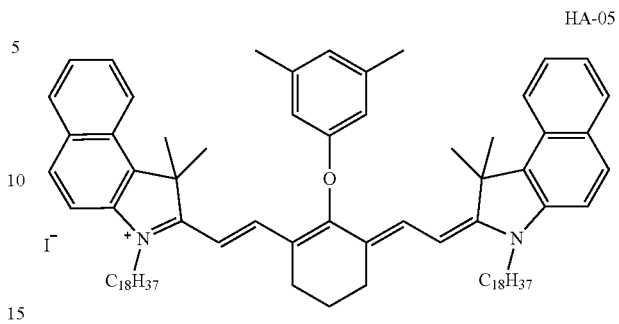

HA-05

The title compound (65%) was prepared from 3,5-dimethylphenol according to the general protocol S1. $^1$H NMR (CD$_3$OD, 400 MHz) δ 0.84-0.88 (t, 6H), 1.25 (s, 55H), 1.44 (br, 12H), 1.84-1.87 (t, 6H), 2.03 (s, 3H), 2.09-2.12 (t, 2H), 2.17 (s, 3H), 2.67 (s, 2H), 2.79 (br, 4H), 4.20-4.24 (t, 4H), 4.60 (s, 1H), 6.18-6.21 (d, 2H, J=14.43 Hz), 6.55 (s, 1H), 6.80-6.82 (d, 1H, J=7.65 Hz), 7.43-7.47 (t, 2H, J=7.15 Hz), 7.53-7.55 (d, 2H, J=8.78 Hz), 7.57-7.66 (m, 3H), 7.94-7.96 (2H, d, J=17.57 Hz), 7.98-8.04 (m, 3H), 8.08-8.10 (2H, J=8.53 Hz). BRMS (ES+), m/z [M+H] 1145.9127.

HA-60-I:

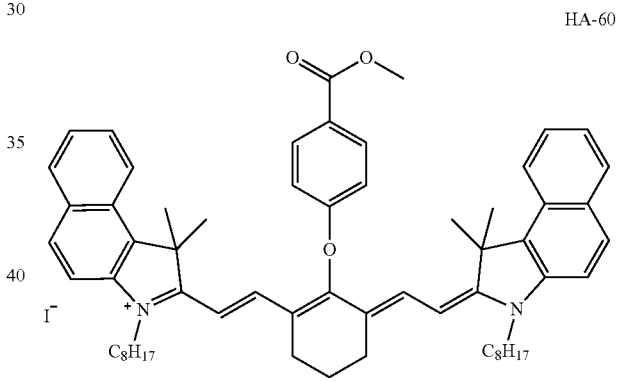

HA-60

Yield (68%) This compound was prepared from methyl-4-hydroxybenzoate and chloro-cyanine C8 according to the general protocol S1. BRMS (ES+), m/z [M+H] 895.5898.

HA-63-I:

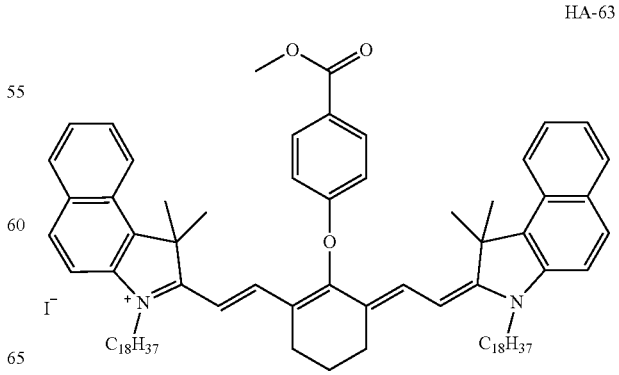

HA-63

Yield (50%). This compound was prepared from methyl-4-hydroxybenzoate and chloro-cyanine C18 according to the general protocol S1. BRMS (ES+), m/z [M+H] 1175.8981.
HA-69-I:

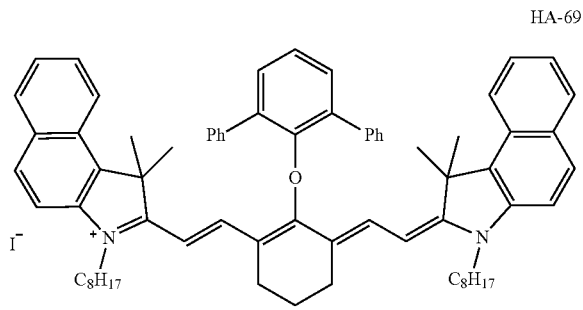

HA-69

The title compound (63%, green solid) was prepared from 3,5-dimethylphenol and chloro-cyanine C8 according to the general protocol S1. $^1$H NMR (CDCl$_3$, 400 MHz) δ 0.87 (s, 6H), 1.16-1.42 (m, 26H), 1.68 (s, 7H), 1.86 (s, 4H), 2.00 (s, 4H), 2.16 (s, 3H), 2.76-2.86 (d, 2H), 4.17-4.29 (d, 4H), 5.49 (s, 3H), 5.94-5.98 (d, 1H, J=13.68 Hz), 6.30-6.33 (1H, d, J=14.18 Hz), 7.30-7.62 (m, 15H), 7.94-8.14 (m, 7H), 8.24-826 (1H, d, J=8.51 Hz), 8.51-8.55 (1H, d, J=14.10 Hz). BRMS (ES+), m/z [M+H] 989.6366.

Tetraphenylborate salts of Cy7.5 derivatives were prepared by the similar protocol as for Cy7.5-C18-TPB.

1.2 Chemical Composition of the Coating Solution

Commercially available poly(methylmethacrylate), Cy7.5-C18-TPB synthesized before, tetraphenylborate and acetonitrile are used for preparing a tested coating solution.

Polymethylmethacrylate is dissolved at 30 mg/ml in acetonitrile. Cy7.5-C18-TPB dye with tetraphenylborate counterion is added at 1 wt % with respect to the polymer.

A comparative coating solution is prepared according to the same protocol. The comparative coating solution is the same as tested coating solution, except that a ICG derivative (ICG, ICG-N, or ICG-P) is used as fluorescent dye in place of Cy7.5-C18-TPB.

ICG-N is an ICG salt with tetrabutyl ammonium as counterion. ICG-P is an ICG salt with tetraphenyl phosphonium as counterion.

These two reference dyes are used to show that counterions in combination with ICG cannot produce the same performance as the specially designed hydrophobic dyes and counterions.

1.3 Protocol of Coating

The coating solution prepared in section 1.2 is placed in the eppendorf tube. The medical device to be coated is immersed into this solution and then immediately taken out by tweezers. It is placed on the aluminium foil to dry for 15-20 min in the dark. Then, the procedure can be repeated 5-10 times in order to increase the thickness of the polymer layer and thus the brightness of the fiducial. After the coating, fiducial is left for 24 h in the dark for complete drying of remaining acetonitrile. At this step the fiducial is ready to use.

A stainless steel wire, silicon pieces, a surgical thread, a catheter, a nano-gastric tube, surgical markers and medical gauze are coated by the tested coating solution according to this protocol.

A stainless steel wire, silicon pieces, a surgical thread are also coated by the comparative coating solutions.

2. Results

Brightness

Compared to ICG-based polymeric coating films, the coating film of the present invention is adhesive to smooth surface, such as on stainless steel wires.

Indeed, the NIR fluorescence of costing film based on Cy7.5-C18-TPB on a stainless steel wire became visible after the first coating and increases by multiple coating, while ICG-based coating films could generate fluorescent labelling of the wires at all even after 5 time coating procedure (FIG. 1).

Stability

The coating film of the present invention is also more stable than ICG-based coating film.

Figure 2:
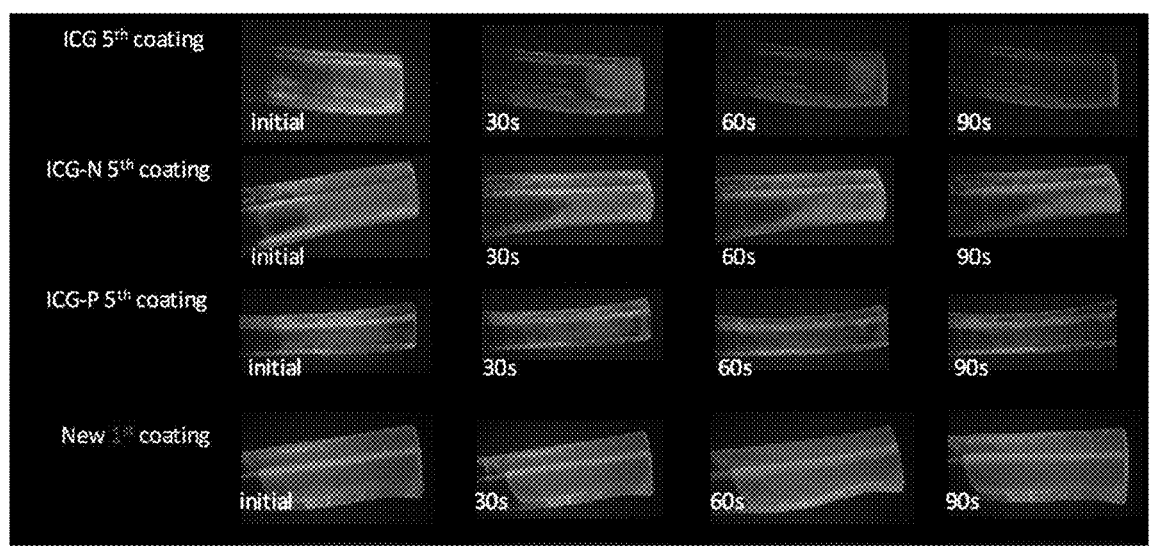
FIG. 2 displays photos by a fluorescent image system of coated silicon pieces taken just after coating procedure (initial, before drying) or after 30 s, 60 s or 90 s of drying. These pieces are respectively coated 1 time by a coating film of the invention (New, Cy7.5-C18-TPB-based coating) or 5 times by three different ICG-based coating films (ICG, ICG-P, ICG-N).

The FIG. 2 shows that fluorescence observed for the coating film of the invention is more homogeneous and can remain stable 90 seconds after the coating procedure, while the fluorescence observed for ICG-based coating films is not homogeneous and is quickly lost.

Figure 3:
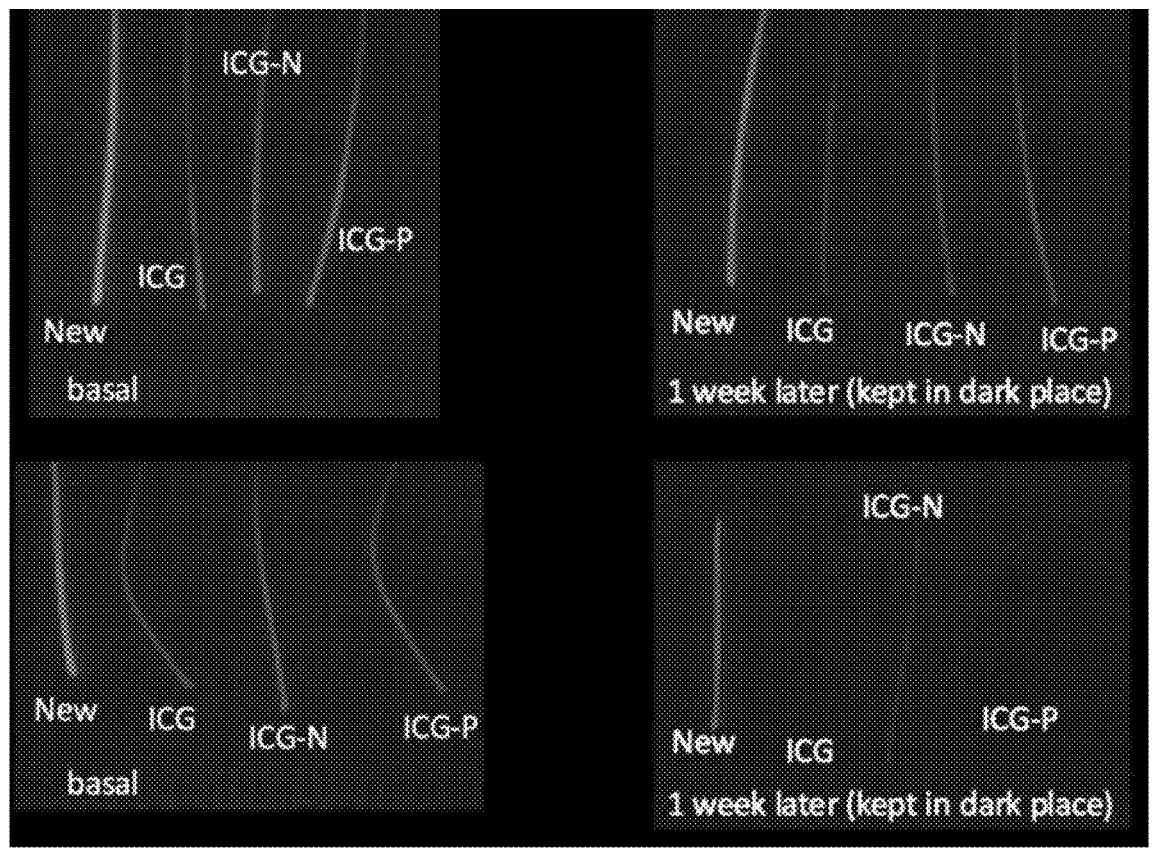
FIG. 3 displays photos of coated surgical thread taken just after coating procedure (basal) or one week after coating by a fluorescent image system. These surgical thread are respectively coated by a coating film of the invention (New, Cy7.5-C18-TPB-based coating) or by ICG-based coating films (ICG, ICG-P, ICG-N).

The FIG. 3 shows that the fluorescence brightness observed for the coating film of the invention on surgical thread is preserved a week after the coating procedure, while the brightness of ICG-based coating films endures significant decrease during 1 week.

It is interesting to note that the presence of a counterion in ICG derivative dyes (ICG-P or ICG-N) does not have significant impact to the brightness and stability of ICG-based polymeric coating films.

In Vivo Application of Coated Surgical Devices

Figure 4:
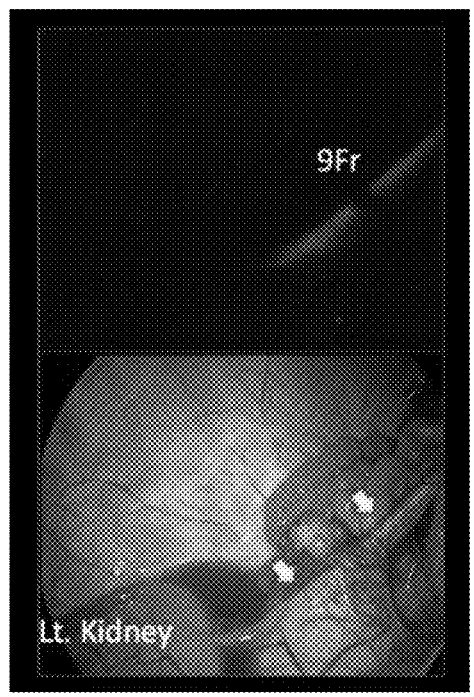
FIG. 4 shows that the ureter (indicated by 2 arrows) during a image-guided surgery is identified by an inserted catheter, which is coated by Cy7.5-C18-TPB-based coating film and visible via fluorescent imaging system.

The FIG. 4 shows that the ureter, which is an anatomical structure vulnerable to injury during lower abdominal operation, can be easily identified by the insertion of a catheter coated by a Cy7.5-C18-TPB-based coating film via a fluorescent imaging system.

Figure 5:
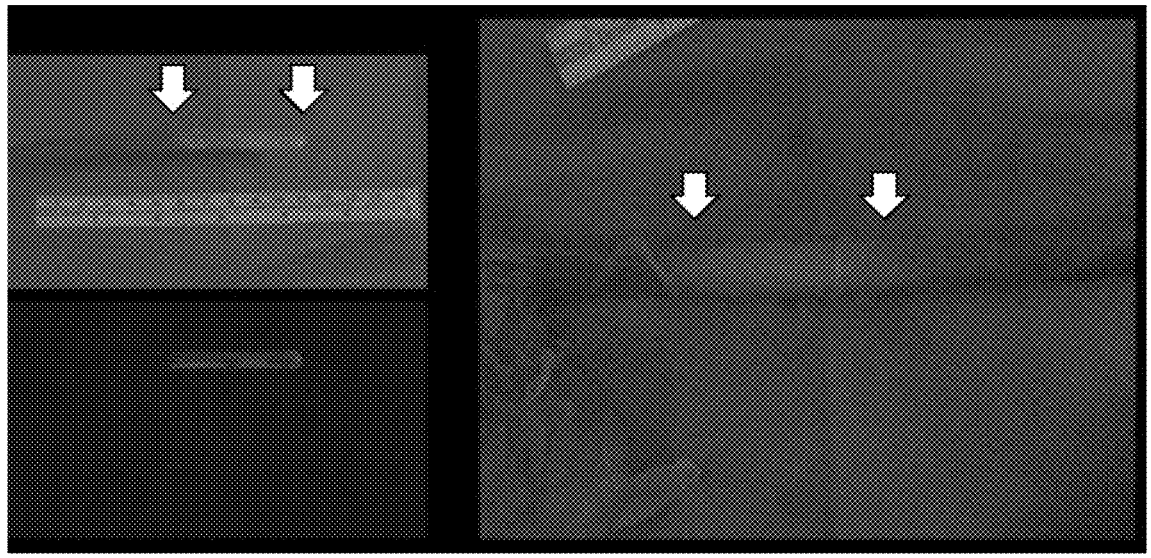
FIG. 5 shows that a tip of naso-gastric tube coated by Cy7.5-C18-TPB-based coating film can be visualized during surgery (indicated by 2 arrows).

The FIG. 5 shows that a tip of naso-gastric tube, which is sometimes difficult to be identified during surgery, can be easily located after being coated by a Cy7.5TPB-based coating film.

Figure 6:
FIG. 6 shows that four-corners of the pathologic lesion of the stomach were marked by insertion of the marker coated by Cy7.5-C18-TPB-based coating film (indicated by 4 arrows).

The FIG. 6 shows that surgical markers coated by a Cy7.5-C18-TPB-based coating film can be visualized from outside of the intestinal organ, which can help the surgeon to find the location of the tumor and be useful for registration of digital augmented reality technology.

Figure 7:
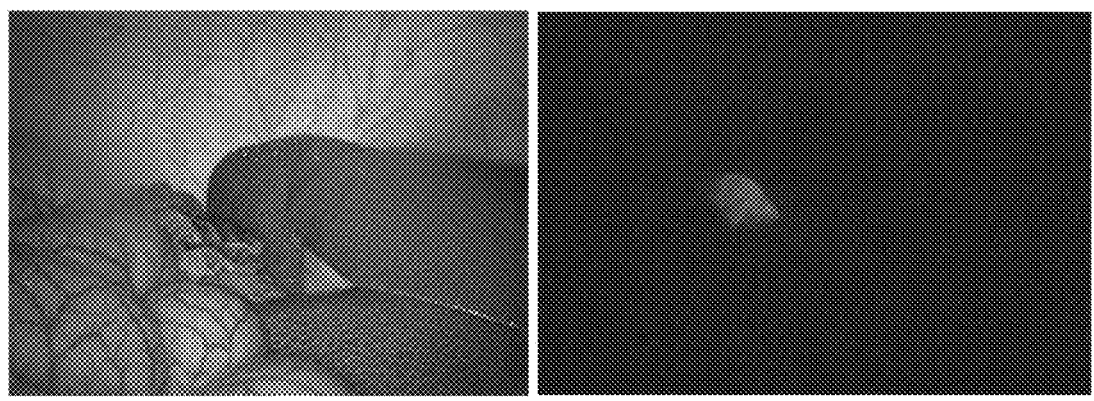
FIG. 7 shows that gauze pieces coated by Cy7.5-C18-TPB-based coating film and plunged by blood during a surgery is identified in NIR via a fluorescent imaging system.

The FIG. 7 shows that the coating film of the present invention can also be used for coating a woven fabric.

Coating of Glass Surface by Films of the Invention

Coating films of the invention containing PMMA and respectively CY7.5-C18-TPB, CY7.5-C8-TPB, HA-60-TPB, or HA-06-I as fluorescent dye and counterion, and comparative coating films containing PMMA with ICG or PMMA only, were prepared by spin coating a mixture of PMMA (30 mg/ml) with different dyes (1% loading) on a 25 mm glass substrate. Images were taken by using a home built NIR imaging setup.

Figure 9:
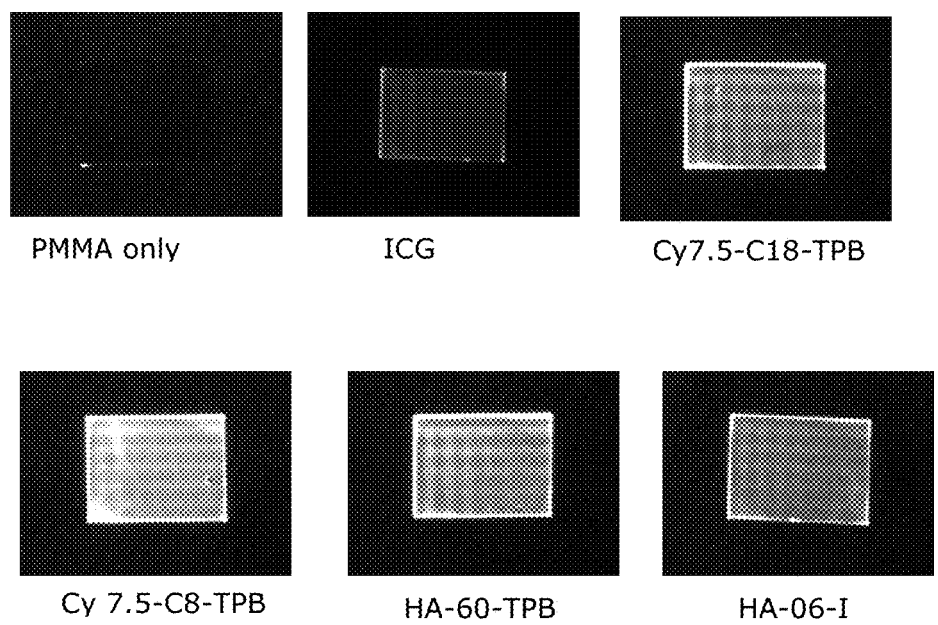
FIG. 9 shows fluorescence images of the coating films containing different dyes of the present invention deposited on the glass surface.

The results illustrated in FIG. 9 show that the coating films of the present invention are brighter than the coating film containing ICG.

Figure 10A:
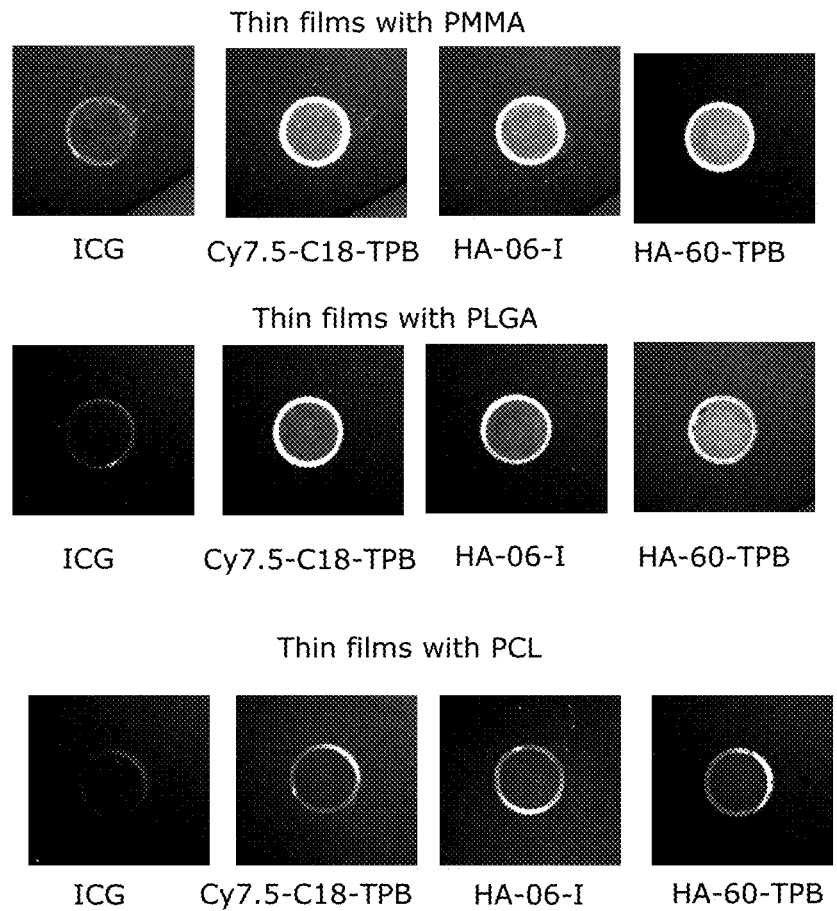
FIG. 10 (A) shows fluorescence images of coating films of the invention based on fluorescent dye CY7.5-C18-TPB, HA-06-I, HA-60-TPB and different hydrophobic polymers: PMMA, PLGA or PLC. The coating films based on ICG are prepared as control.
Figure 10B:
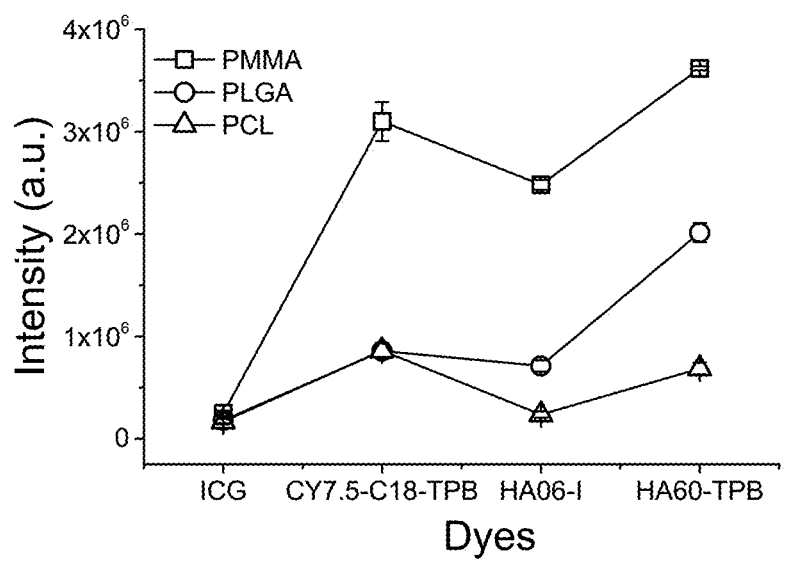
Figure 11:
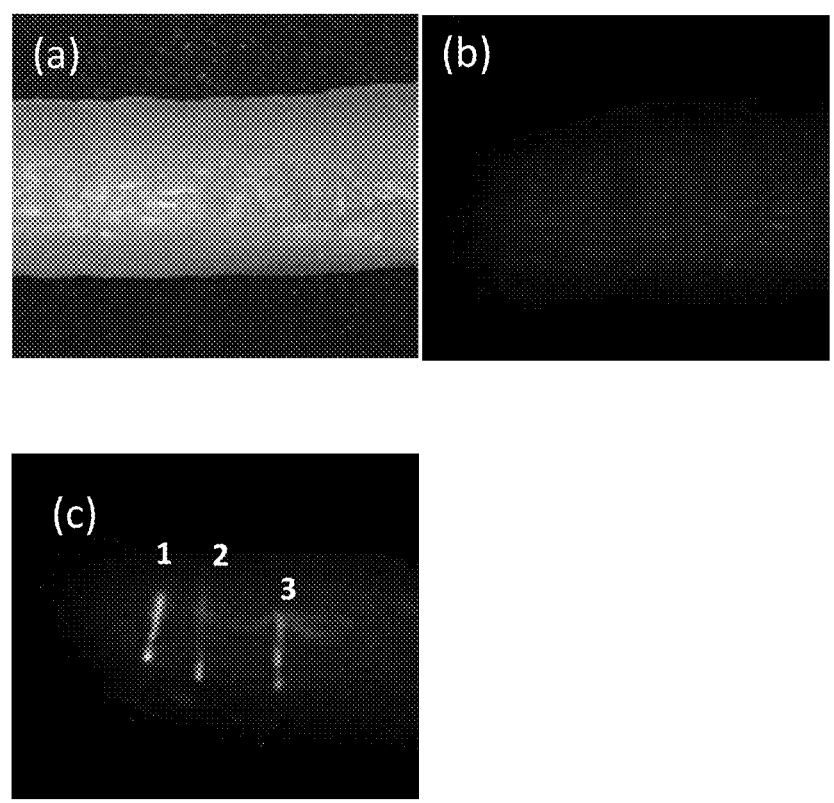
FIG. 11 shows tissue imaging with steel fiducials coated with different dyes (1% loading) in PMMA: (a) Chicken tissue under normal light; (b) fluorescence image of the tissue; (c) Fluorescence images of the coated fiducials inserted into the chicken tissues (1 for HA-06-I, 2 for HA-60-TPB, 3 for Cy7.5-C18-TPB).

Coating films made from different polymers were also tested. For all studied polymers, coating films based on fluorescent dyes Cy7.5-C18-TPB and the derivatives HA-06-I, HA-60-TPB systematically display better brightness than a coating film based on ICG (FIG. 10A, 10B).

Moreover, the NIR fluorescence detected from steel fiducials coated with PMMA films based on HA-06-I or HA-60-TPB inserted into muscle tissue is comparable with that from coating PMMA film based on CY7.5-C18-TPB (FIG. 11).

The invention claimed is:

1. A fluorescent polymeric coating film visible in near-infrared light for coating a medical device, said coating film being a single layer or multiple layers, wherein said single layer or at least one layer of said multiple layers comprises a hydrophobic polymer, an ionic fluorescent dye and a counterion of said ionic fluorescent dye, said ionic fluorescent dye being represented by Formula I

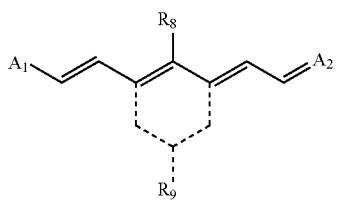

(Formula I)

wherein:
the dash line represents a C6-cyclic structure which is present or absent, and $R_9$ is present when the C6-cyclic structure is present and $R_9$ is absent when the C6-cyclic structure is absent, $R_8$ and $R_9$ are the same or different and independently selected from the group consisting of:
an hydrogen,
a group chosen from a (C1-C20)alkyl, a cyclo(C3-C20)alkyl, a (C2-C20)alkenyl, a (C2-C20)alkynyl, a heterocyclic group, a cyclo(C3-C20)alkenyl, a heterocyclo(C2-C20)alkenyl, an aryl, a heteroaryl, a hetero (C1-C20)alkyl, a (C1-C20)alkylaryl, or a (C1-C20)alkylheteroaryl, said group being unsubstituted or substituted by one or two substituents chosen from a (C1-C5) alkyl, an aryl, and —COOR$_{11}$, $R_{11}$ being a (C1-C20)alkyl,
a group of formula —(E-R$_{10}$, wherein E is chosen from —O—, —S—, —Se—, —NH—, and —CH$_2$—; $R_{10}$ is chosen from a (C1-C20)alkyl, a cyclo(C3-C20)alkyl, a (C2-C20)alkenyl, a (C2-C20)alkynyl, a heterocyclic group, a cyclo(C3-C20)alkenyl, a heterocyclo(C2-C20)alkenyl, an aryl, a heteroaryl, a hetero (C1-C20)alkyl, a (C1-C20)alkylaryl, a (C1-C20)alkylheteroaryl, $R_{10}$ being unsubstituted or substituted by one to three substituents chosen from a (C1-C5) alkyl, an aryl, and —COOR$_{11}$, $R_{11}$ being a (C1-C20) alkyl;

$A_1$ is

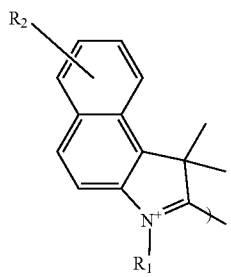

and $A_2$ is

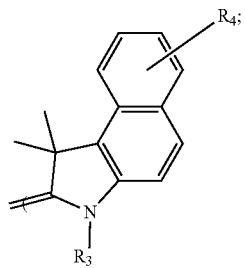

or $A_1$ is

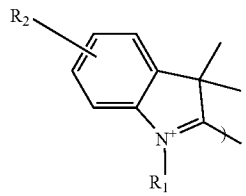

and $A_2$ is

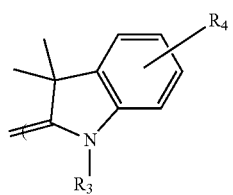

Wherein:
$R_2$ and $R_4$ are independently selected from the group consisting of hydrogen, halogen, (C1-C10) alkyl, —OR$_5$, —NR$_5$R$_6$, —NO$_2$, —CF$_3$, —CN, —SR$_5$, —N$_3$, —C(=O)R$_5$, —OC(=O)OR$_5$, and —C(=O)NR$_5$R$_6$, —NR$_5$C(=O)R$_6$, wherein R$_5$ and R$_6$ are independently selected from hydrogen, unsubstituted (C1-C10)alkyl, unsubstituted (C2-C10)alkenyl, unsubstituted (C2-C10)alkynyl, cyclo(C3-C10)alkyl, heterocyclic group, cyclo(C3-C10)alkenyl, heterocyclo (C2-C10)alkenyl, aryl, heteroaryl, aryl(C1-C10)alkyl, hetero(C1-C10)alkyl, (C1-C10)alkylaryl, and (C1-C10)alkylheteroaryl;

$R_1$ and $R_3$ are independently selected from the group consisting of a (C1-C20)alkyl unsubstituted or substituted by a hydrophobic group, a cyclo(C3-C20)alkyl unsubstituted or substituted by a hydrophobic group, a (C2-C20)alkenyl unsubstituted or substituted by a hydrophobic group, a (C2-C20)alkynyl, a heterocyclic group unsubstituted or substituted by a hydrophobic group, a cyclo(C3-C20)alkenyl unsubstituted or substituted by a hydrophobic group, a heterocyclo(C2-C20)alkenyl unsubstituted or substituted by a hydrophobic group, an aryl unsubstituted or substituted by a hydrophobic group, a heteroaryl unsubstituted or substituted by a hydrophobic group, a hetero(C1-C20)alkyl unsubstituted or substituted by a hydrophobic group, a (C1-C20)alkylaryl unsubstituted or substituted by a hydrophobic group, and a (C1-C20)alkylheteroaryl unsubstituted or substituted by a hydrophobic group, said hydrophobic group being selected from methyl, ethyl, methoxy, and ethyloxy;

said hydrophobic polymer is chosen from poly(methyl methacrylate), poly(ethyl methacrylate), poly(propyl methacrylate), poly(butyl methacrylate), poly(methyl methacrylate-co-methacrylic acid), poly(lactide-co-glycolide), polylactic acid, polyglycolic acid, polycaprolacton, cellulose triacetate, nitrocellulose, polydimethylsiloxane, poly(ethylene terephthalate), polycarbonate, polyethylene, ethylene vinyl acetate copolymer, polyurethane, polystyrene, and copolymers thereof with poly(ethylene glycol), wherein said counterion is a bulky organic counterion chosen from tetraphenylborate, tetrakis(pentafluorophenyl)borate, tetrakis(4-fluorophenyl)borate, tetrakis[3,5-bis-(trifluoromethyl)phenyl]borate, tetrakis[3,5-bis-(1,1,1,3,3,3-hexafluoro-2-methoxy-2-propyl)phenyl]borate and tetrakis[perfluoro-tert-butoxy]aluminate.

2. The fluorescent polymeric coating film according to claim 1, said ionic fluorescent dye being represented by Formula I

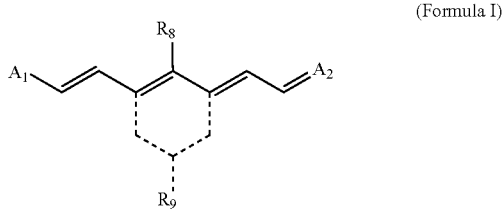

(Formula I)

wherein:
the dash line represents a C6-cyclic structure which is present or absent, and $R_9$ is present when the C6-cyclic structure is present and $R_9$ is absent when the C6-cyclic structure is absent, $R_8$ and $R_9$ are the same or different and independently selected from the group consisting of an hydrogen, an unsubstituted (C1-C20)alkyl, an unsubstituted cyclo(C3-C20)alkyl, an unsubstituted (C2-C20)alkenyl, an unsubstituted (C2-C20)alkynyl, an unsubstituted heterocyclic group, an unsubstituted cyclo(C3-C20)alkenyl, an unsubstituted heterocyclo(C2-C20)alkenyl, an unsubstituted aryl, an unsubstituted heteroaryl, an unsubstituted hetero(C1-C20)alkyl, an unsubstituted (C1-C20)alkylaryl, and an unsubstituted (C1-C20)alkylheteroaryl;

$A_1$ is

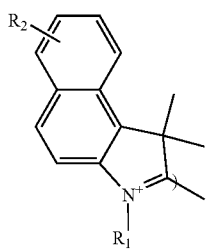

and $A_2$ is

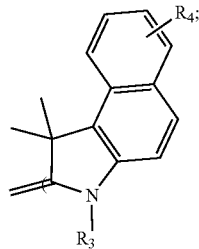

or $A_1$ is

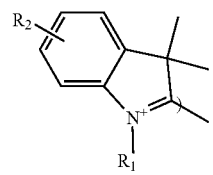

and $A_2$ is

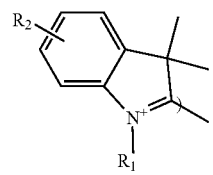

Wherein:
$R_2$ and $R_4$ are independently selected from the group consisting of hydrogen, halogen, (C1-C10)alkyl, —$OR_5$, —$NR_5R_6$, —$NO_2$, —$CF_3$, —CN, —$SR_5$, —$N_3$, —C(=O)$R_5$, —OC(=O)$OR_5$, —C(=O)$NR_5R_6$, and —$NR_5$C(=O)$R_6$, wherein $R_5$ and $R_6$ are independently selected from hydrogen, unsubstituted (C1-C10) alkyl, unsubstituted (C2-C10)alkenyl, unsubstituted (C2-C10)alkynyl, cyclo(C3-C10)alkyl, heterocyclic group, cyclo(C3-C10)alkenyl, heterocyclo(C2-C10) alkenyl, aryl, heteroaryl, aryl(C1-C10)alkyl, hetero (C1-C10)alkyl, (C1-C10)alkylaryl, and (C1-C10)alkylheteroaryl;

$R_1$ and $R_3$ are independently selected from the group consisting of a (C1-C20)alkyl unsubstituted or substituted by a hydrophobic group, a cyclo(C3-C20)alkyl unsubstituted or substituted by a hydrophobic group, a (C2-C20)alkenyl unsubstituted or substituted by a hydrophobic group, a (C2-C20)alkynyl, a heterocyclic group unsubstituted or substituted by a hydrophobic group, a cyclo(C3-C20)alkenyl substituted or substituted by a hydrophobic group, a heterocyclo(C2-C20) alkenyl unsubstituted or substituted by a hydrophobic group, an aryl unsubstituted or substituted by a hydrophobic group, a heteroaryl unsubstituted or substituted by a hydrophobic group, a hetero(C1-C20)alkyl unsubstituted or substituted by a hydrophobic group, a (C1-C20)alkylaryl eventually substituted by a hydrophobic group, and a (C1-C20)alkylheteroaryl unsubstituted or substituted by a hydrophobic group, said hydrophobic group being selected from methyl, ethyl, methoxy, and ethyloxy.

3. The fluorescent polymeric coating film according to claim 1, wherein $A_1$ is

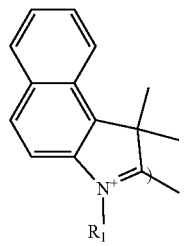

and $A_2$ is

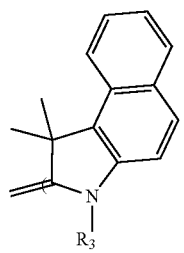

$R_1$ and $R_3$ being defined in claim 1.

4. The fluorescent polymeric coating film according to claim 1, wherein $R_1$ and $R_3$ are independently selected from the group consisting of unsubstituted (C1-C20)alkyl, an unsubstituted cyclo(C3-C20)alkyl, an unsubstituted (C2-C20)alkenyl, an unsubstituted (C2-C20)alkynyl, an unsubstituted heterocyclic group, an unsubstituted cyclo(C3-C20) alkenyl, an unsubstituted heterocyclo(C2-C20)alkenyl, an unsubstituted aryl, an unsubstituted heteroaryl, an unsubstituted hetero(C1-C20)alkyl, an unsubstituted (C1-C20)alkylaryl, and an unsubstituted (C1-C20)alkylheteroaryl.

5. The fluorescent polymeric coating film according to claim 4, wherein $R_1$ and $R_3$ are independently unsubstituted (C8-C20)akyls.

6. The fluorescent polymeric coating film according to claim 1, wherein the ionic fluorescent dye is of Formula Ia

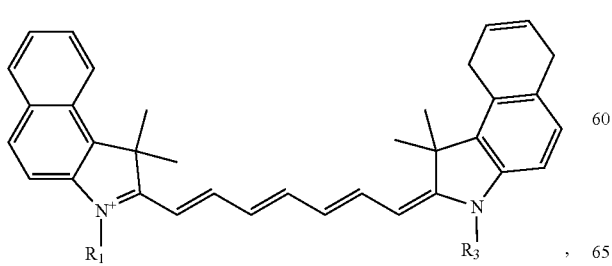

(Formula Ia)

or of Formula Ib

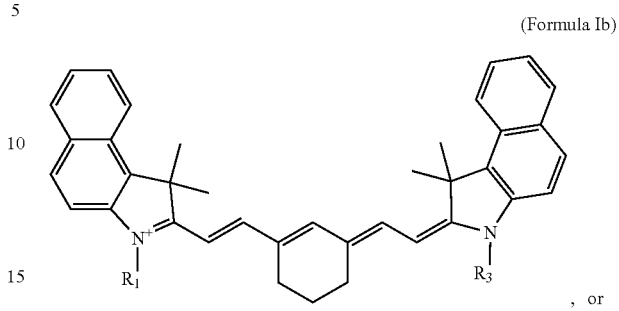

(Formula Ib)

, or

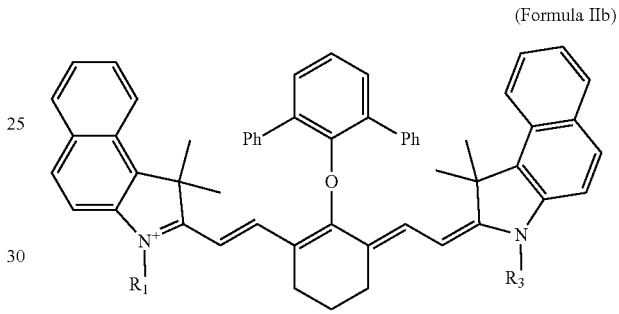

(Formula IIb)

wherein $R_1$ and $R_3$ are independently selected from the group consisting of unsubstituted (C1-C20)alkyl, an unsubstituted cyclo(C3-C20)alkyl, an unsubstituted (C2-C20)alkenyl, an unsubstituted (C2-C20)alkynyl, an unsubstituted heterocyclic group, an unsubstituted cyclo(C3-C20)alkenyl, an unsubstituted heterocyclo(C2-C20)alkenyl, an unsubstituted aryl, an unsubstituted heteroaryl, an unsubstituted hetero (C1-C20)alkyl, an unsubstituted (C1-C20)alkylaryl, and an unsubstituted (C1-C20)alkylheteroaryl.

7. The fluorescent polymeric coating film according to claim 1, wherein the ionic fluorescent dye is

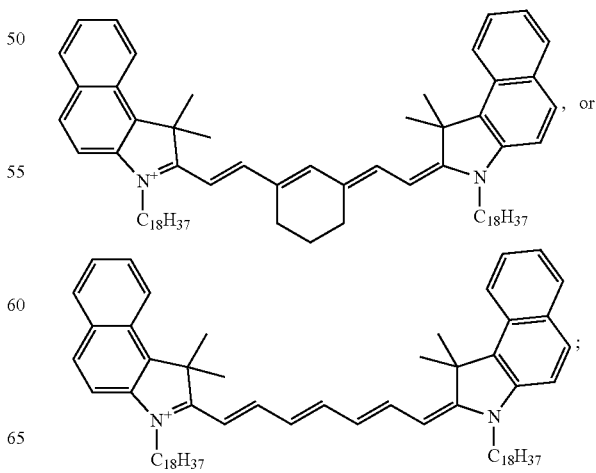

33
-continued

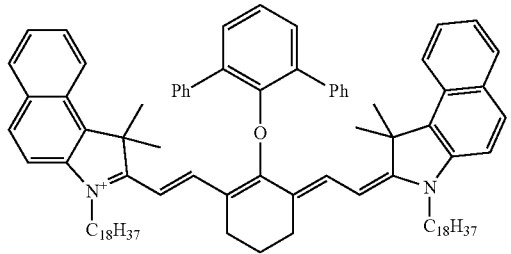

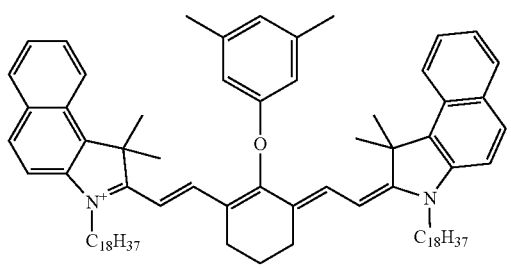

34
-continued

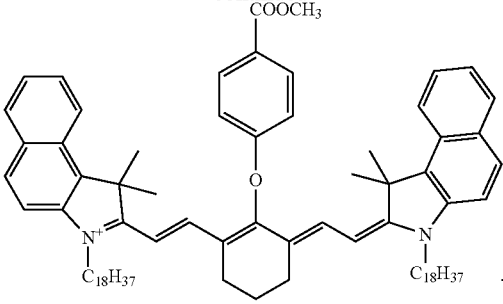

8. The fluorescent polymeric coating film according to claim 1, wherein the weight of said ionic fluorescent dye in said layer is from 0.1 to 50%, by weight of the hydrophobic polymer in said layer.

9. The fluorescent polymeric coating film according to claim 2, wherein the hydrophobic polymer is a biocompatible hydrophobic polymer.

10. The fluorescent polymeric coating film according to claim 5, wherein $R_1$ and $R_3$ are independently selected from the group of unsubstituted (C12-C18)alkyl.

11. The fluorescent polymeric coating film according to claim 1, wherein R8 is a group of formula $-(E-R_{10}$, wherein E is chosen from —O—, —S—, —Se—, —NH—, and —CH$_2$—; and R10 is a phenyl being substituted by one to three substituents chosen from a (C1-C5)alkyl, an aryl, and —COOR11, R11 being a (C1-C20) alkyl.

* * * * *